US006291725B1

(12) United States Patent
Chopade et al.

(10) Patent No.: US 6,291,725 B1
(45) Date of Patent: Sep. 18, 2001

(54) CATALYSTS AND PROCESS FOR HYDROGENOLYSIS OF SUGAR ALCOHOLS TO POLYOLS

(75) Inventors: Shubham P. Chopade, East Lansing; Dennis J. Miller, Okemos; James E. Jackson, Haslett, all of MI (US); Todd A. Werpy, West Richland, WA (US); John G. Frye, Jr.; Alan H. Zacher, both of Richland, WA (US)

(73) Assignees: Board of Trustees operating Michigan State University, East Lansing, MI (US); Battelle Memorial Institute, Pacific Northwest Laboratory, Richland, WA (US)

( * ) Notice: Subject to any disclaimer, the term of this patent is extended or adjusted under 35 U.S.C. 154(b) by 0 days.

(21) Appl. No.: 09/518,860

(22) Filed: Mar. 3, 2000

(51) Int. Cl.⁷ ............................. C07C 31/18; C07C 29/60
(52) U.S. Cl. ..................... 568/861; 568/862; 568/863; 568/864
(58) Field of Search ..................................... 568/861, 862, 568/863, 864

(56) References Cited

U.S. PATENT DOCUMENTS

| | | |
|---|---|---|
| 1,963,997 | 6/1934 | Larchar . |
| 2,004,135 | 6/1935 | Rothrock . |
| 2,852,570 | 9/1958 | Conradin et al. . |
| 3,030,429 | 4/1962 | Conradin et al. . |
| 3,396,199 | 8/1968 | Kasehagen . |
| 4,338,472 | 7/1982 | Sirkar . |
| 4,366,332 | 12/1982 | Chao et al. . |
| 4,380,675 | 4/1983 | Gebauer et al. . |
| 4,401,823 | 8/1983 | Arena . |
| 4,404,411 | 9/1983 | Tanikella . |
| 4,430,253 | 2/1984 | Dubeck et al. . |
| 4,496,780 | 1/1985 | Arena . |
| 4,552,862 * | 11/1985 | Larkin ................................... 502/306 |
| 5,026,927 | 6/1991 | Andrews et al. . |
| 5,210,335 | 5/1993 | Schuster et al. . |
| 5,326,912 | 7/1994 | Gubitosa et al. . |
| 5,354,914 | 10/1994 | Gubitosa et al. . |
| 5,600,028 | 2/1997 | Gubitosa et al. . |

OTHER PUBLICATIONS

Van Ling and Vlugter, J. Appl. Chem. 19:43 (1969).
Muller et al in Heterogeneous Catalysis and Fine Chemicals II, M. Guisnet et al, eds. Elsevier Press, Amsterdam, Netherlands, p. 237 (1991).
Montassier et al., J. Mole. Catal. 70: 99 (1991).
Brunauer, emmett, and Teller (BET), J. Am. Chem. Soc., 60:309 (1938).

* cited by examiner

Primary Examiner—Johann Richter
Assistant Examiner—Brian J. Davis
(74) Attorney, Agent, or Firm—Ian C. McLeod

(57) ABSTRACT

The present invention provides a process for preparation of low molecular weight polyols from high molecular weight polyols in a hydrogenolysis reaction under elevated temperature and hydrogen pressure. The process comprises providing in a reaction mixture the polyols, a base, and a metal catalyst prepared by depositing a transition metal salt on an inert support, reducing the metal salt to the metal with hydrogen, and passivating the metal with oxygen, and wherein the catalyst is reduced with hydrogen prior to the reaction. In particular, the process provides for the preparation of glycerol, propylene glycol, and ethylene glycol from sugar alcohols such as sorbitol or xylitol. In a preferred process, the metal catalyst comprises ruthenium which is deposited on an alumina, titania, or carbon support, and the dispersion of the ruthenium on the support increases during the hydrogenolysis reaction.

23 Claims, 3 Drawing Sheets

CATALYSTS AND PROCESS FOR HYDROGENOLYSIS OF SUGAR ALCOHOLS TO POLYOLS

STATEMENT REGARDING FEDERALLY SPONSORED RESEARCH OR DEVELOPMENT

This invention was supported by U.S. Department of Energy Contract No. DE-AC06-76RLO1830. The U.S. Government has certain rights in the invention.

CROSS-REFERENCE TO RELATED APPLICATION

None.

BACKGROUND OF THE INVENTION

(1) Field of the Invention

The present invention relates to a process for preparation of low molecular weight polyols from high molecular weight polyols in a hydrogenolysis reaction under elevated temperature and hydrogen pressure which comprises providing in a reaction mixture the polyols, a base, and a metal catalyst prepared by depositing a transition metal salt on an inert support, reducing the metal salt to the metal with hydrogen, and passivating the metal with oxygen, and wherein the catalyst is reduced with hydrogen prior to the reaction. In particular, the process relates to the preparation of glycerol, propylene glycol, and ethylene glycol from sugar alcohols such as sorbitol or xylitol. In a preferred process, the catalyst comprises ruthenium deposited on an alumina, titania, or carbon support, and the dispersion of the ruthenium on the support increases during the hydrogenolysis reaction.

(2) Description of Related Art

Hydrogenolysis processes for cleavage of C—C and C—O bonds was first applied to oxygenated organic compounds in the 1930s. Since then, the majority of publications and patents relating to hydrogenolysis have focused on C6 sugar alcohols such as glucose and sorbitol as substrates for hydrogenolysis. In contrast, very few studies on hydrogenolysis have been concerned with C5 substrates such as xylose and xylitol.

In the prior art, conditions for sorbitol hydrogenolysis have involved a supported metal catalyst, a base promoter such as CaO or KOH, temperatures of about 180° C. to 250° C., and elevated hydrogen pressures (4 to 20 MPa). In early work, Ni/kieselguhr catalysts were shown to achieve 40% by weight yields of glycerol, 17% propylene glycol, and 16% ethylene glycol (Clark, Ind. and Eng. Chem. 50: 1125 (1958)). Propylene glycol and ethylene glycol were formed via secondary reactions on glycerol indicating that the C3–C4 bond cleavage was the primary mechanism in the hydrogenolysis of sorbitol. When Van Ling and Vlugter (J. Appl. Chem. 19: 43 (1969)) used ceria-promoted copper on silica catalysts, C3–C4 sorbitol selectivities of 65% to 70% were achieved. Using a Ru/C catalyst and sucrose as the reactant, Muller et al. in *Heterogeneous Catalysis and Fine Chemicals* II (M. Guisnet et al., eds.) Elsevier Press, Amsterdam, Netherlands, p 237 (1991) achieved a propylene glycol yield of 46% with 55% selectivity. Further, Montassier et al. (J. Mole. Catal. 70: 99 (1991)) were able to convert sorbitol and xylitol to desired products over both ruthenium on carbon support catalysts and sulfur-modified ruthenium on carbon support catalysts. They were able to obtain selectivities of 64% for C3–C4 cleavages of sorbitol, and 86% for C2–C3 cleavages of xylitol.

A number of patents have been issued regarding catalysts and processes for sorbitol and xylitol hydrogenolysis. Most noteworthy are U.S. Pat. No. 4,430,253 to Dubeck wherein S-modified (sulfided) ruthenium on carbon catalysts were disclosed in which 96% of the carbon in sorbitol was converted to propylene glycol, ethylene glycol, and glycerol; U.S. Pat. Nos. 4,401,823 and 4,496,780 to Arena wherein ruthenium/barium oxide on $Al_2O_3$ catalysts were disclosed which achieved a 75% selectivity to propylene glycol and glycerol from sorbitol; U.S. Pat. No. 5,210,335 to Schuster et al. wherein $Co/Cu/MnO_x$ mixed metal oxide catalysts produced propylene glycol yields of 50 to 65%; and, U.S. Pat. No. 5,600,028 to Gubitosa et al. which disclosed a method for producing lower polyhydric alcohols such as glycerol from higher polyhydric alcohols such as sorbitol using a catalyst consisting of ruthenium on activated carbon with a BET surface area from 600 to 1,000 $m^2$ per gram.

Other U.S. patents that disclose catalysts for hydrogenolysis reactions are U.S. Pat. No. 1,963,997 to Larchar and U.S. Pat. No. 2,004,135 to Rothrock which disclosed a Ni—$CrO_x$ catalyst that was useful for converting sorbitol to polyethylene glycol; U.S. Pat. Nos. 2,852,570 and 3,030,429 to Conradin et al. which disclosed a hydrogenolysis reaction using Cu-MgO-Ni catalysts in 16 MPa $H_2$ at 220° C. that yielded 35% glycerol and 30% ethylene glycol from sorbitol; U.S. Pat. No. 3,396,199 to Kasehagen which disclosed a hydrogenolysis reaction using a Ni on diatomaceous earth catalyst in 13 MPa $H_2$ with an overall 69% conversion of sorbitol with 60% selectivity to glycerol; U.S. Pat. Nos. 4,338,472, 4,366,332, and 4,380,675 to Chao et al. which disclosed hydrogenolysis reactions using a $Ni/SiO_2$ catalyst with a CaO promoter which produced yields from sorbitol of 27% glycerol, 25% propylene glycol, and 19% ethylene glycol; U.S. Pat. No. 4,404,411 to Tanikella which disclosed a hydrogenolysis reaction conducted in a batch reactor at 13 to 40 MPa hydrogen pressure that yielded 35% ethylene glycol, 40% propylene glycol, and 4% glycerol from xylitol using a Ni on $SiAlO_x$ catalyst in methanol and an alkali alkoxide promoter; U.S. Pat. No. 5,026,927 to Andrews et al. which disclosed a hydrogenolysis reaction that yielded 36% glycerol and 8% ethylene glycol from sorbitol using a $H_2Ru(PPh_3)_4$ with KOH in NMP; and, U.S. Pat. Nos. 5,326,912 and 5,354,914 to Gubitosa et al. which disclosed ruthenium-based catalysts such as Ru/Cu/Pd/Pt on carbon and Ru/Sn on carbon that yielded 48% propylene glycol, 18% ethylene glycol, and 6% glycerol from sorbitol.

In general, the prior art processes use catalysts that require special handling procedures to prevent destruction of the catalyst. Furthermore, these catalysts have a relatively short useful life which limits the duration of the hydrogenolysis. Therefore, there is a need for a process that uses a catalyst which can be stored under atmospheric conditions, has a longer useful life during the hydrogenolysis reaction, and improves the overall selectivity of hydrogenolysis to desired products under mild conditions.

SUMMARY OF THE INVENTION

The present invention provides a process for conversion of sugar alcohols, also known as high molecular weight polyols, to low molecular weight polyols with high selectivity and yield. The process is a hydrogenolysis reaction that uses a catalyst comprising a transition metal, preferably ruthenium, deposited on an inert support wherein the support has a large micropore volume which facilitates with high selectivity, conversion of sugar alcohols to low molecular weight polyols such as ethylene glycol, propylene glycol, and glycerol.

A remarkable property of the catalyst of the present invention is that as the conversion reaction proceeds, there is a corresponding increase in the dispersion of the metal on the catalyst. The increased dispersion of the metal extends the active life of the catalyst by continuously making more of the metal available for catalyzing the reaction. Thus, the present invention provides a process and catalyst for converting C5 and C6 sugar alcohols, including but not limited to, xylitol, arabinitol, and sorbitol derived from corn fiber hydrolysates, to low molecular weight polyols.

Therefore, the present invention provides a process for preparation of low molecular weight polyols which comprises: (a) providing a transition metal catalyst prepared by depositing a transition metal salt in a solvent on an inert support, drying to remove the solvent, reducing the metal salt to the metal with hydrogen, and passivating the metal in an oxygen containing atmosphere so as to provide an oxide of the metal on the surface of the metal in a reaction vessel; (b) reacting the catalyst with hydrogen in the vessel; (c) providing to the vessel a reaction mixture of a high molecular weight polyol in water and a base promoter; (d) reacting the reaction mixture containing the base with the catalyst at elevated temperature and hydrogen pressure wherein the temperature is between 180° C. and 250° C. and the hydrogen pressure is between about 3.4 to 14 MPa (500 to 2,000 PSIG) to produce low molecular weight polyols in the reaction mixture; (e) removing the reaction mixture with the lower molecular weight polyols from the vessel; and, (f) recovering the low molecular weight polyols from the reaction mixture. In a preferred process, the inert support is selected from the group consisting of alumina, titania, and microporous carbon. Furthermore, it is preferred that the transition metal is ruthenium.

The present invention also provides a process for preparation of a mixture of ethylene glycol and propylene glycol which comprises: (a) providing a ruthenium metal catalyst prepared by depositing a ruthenium metal salt in a solvent on an inert support, drying to remove the solvent, reducing the ruthenium salt to ruthenium metal with hydrogen, and passivating the ruthenium metal in an oxygen containing atmosphere so as to provide an oxide of the metal on the surface of the metal in a reaction vessel; (b) reacting the catalyst with hydrogen in the vessel; (c) providing to the vessel a reaction mixture of a high molecular weight polyol in water and a base promoter; (d) reacting in the vessel the reaction mixture containing the base with the catalyst at elevated temperature and hydrogen pressure, wherein the base is present in an amount between 0.02 and 0.3 moles per liter, the pressure is between about 3.4 to 14 MPa (500 to 2,000 PSIG), the mixture of polyols is between 5% to 70% by weight in water, the temperature is between 180° C. and 250° C. to produce the ethylene glycol and propylene glycol in the reaction mixture; (e) removing the reaction mixture with the lower molecular weight polyols from the vessel; and, (f) recovering the low molecular weight polyols from the reaction mixture.

In a preferred embodiment of the above process, the vessel is sealed. Further, in the process wherein the vessel is sealed, the vessel can be a column with continuous flow through the column of the reaction mixture over the catalyst wherein a weight hourly space velocity is between about 0.3 and 3. And further still in the above process, the ratio of hydrogen to polyols is between about 1.4 to 1 and 8.7 to 1 in the sealed reaction vessel.

In a preferred embodiment of the above process, the inert support is microporous carbon that preferably has a greater than 0.6 cc per gram of microporous void volume. A particularly desirable microporous carbon is derived from coconut shells.

Further, in the present invention, the base promoter is selected from the group consisting of alkali metals and bases. In a preferred embodiment, the base promoter is selected from the group consisting of potassium hydroxide, sodium formate, sodium hydroxide, or sodium carbonate.

In particular embodiments of the process of the present invention, upon removal of the reaction mixture from the vessel, the reaction mixture is introduced into a separator for separating liquids from gases generated during the reaction and the hydrogen, which gases are then separated from the hydrogen with return of the hydrogen to the reaction mixture, and wherein the removed liquid is demineralized to remove inorganic components and recovering ethylene glycol, propylene glycol, and glycerol from the liquid.

Further, in the process of the present invention, some water is removed from the liquid upon removal of the ethylene glycol and propylene glycol to produce a recycle mixture which is added to the reaction mixture along with the base.

Therefore, the present invention provides a process for preparation of low molecular weight polyols which comprises (a) providing a transition metal catalyst prepared by depositing a transition metal salt in a solvent on an inert support, drying to remove the solvent, reducing the metal salt to the metal with hydrogen, and passivating the metal in an oxygen containing atmosphere so as to provide an oxide of the metal on the surface of the metal in a reaction vessel; (b) reacting the passivated catalyst with hydrogen in the vessel; (c) providing to the vessel a reaction mixture of a high molecular weight polyol in water and a base promoter; (d) reacting the reaction mixture containing the base with the catalyst at elevated temperature and elevated hydrogen pressure to produce low molecular weight polyols in the reaction mixture; (e) removing the reaction mixture with the lower molecular weight polyols from the vessel; and, (f) recovering the low molecular weight polyols from the reaction mixture.

And, in a preferred embodiment, the present invention provides a process for preparation of low molecular weight polyols which comprises: (a) providing a passivated transition metal catalyst comprising a transition metal on an inert support wherein the dispersion of the transition metal increases over time in a hydrogenolysis reaction in a reaction vessel; (b) reacting the passivated catalyst with hydrogen in the vessel; (c) providing to the vessel a reaction mixture of a high molecular weight polyol in water and a base promoter; (d) reacting the reaction mixture containing the base with the catalyst at elevated temperature and elevated hydrogen pressure to produce low molecular weight polyols in the reaction mixture; (e) removing the reaction mixture with the lower molecular weight polyols from the vessel; and, (f) recovering the low molecular weight polyols from the reaction mixture. In a preferred embodiment, the passivated transition metal catalyst is prepared by depositing a transition metal salt in a solvent on an inert support, drying to remove the solvent, reducing the metal salt to the metal with hydrogen, and passivating the metal in an oxygen containing atmosphere so as to provide an oxide of the metal on the surface of the metal. It is preferable that the inert support is selected from the group consisting of alumina, titania, and microporous carbon. In particular, it is preferred that the inert support has a BET surface area between about 1 to 1,000 m² per gram. In a most preferred embodiment, the transition metal is ruthenium at between about 1.5 to 5.0 wt %.

Therefore, it is an object of the present invention to provide a process for the conversion of sugar alcohols or high molecular weight polyols to value-added polyols with high selectivity by hydrogenolysis over supported metal catalysts in both batch reactions and continuous fixed-bed reactions. It is also an object of the present invention to provide a process for the hydrogenolysis of C5 and C6 sugar alcohols.

These and other objects will become increasingly apparent by reference to the following description and drawings.

DESCRIPTION OF PREFERRED EMBODIMENTS

Figure 1:
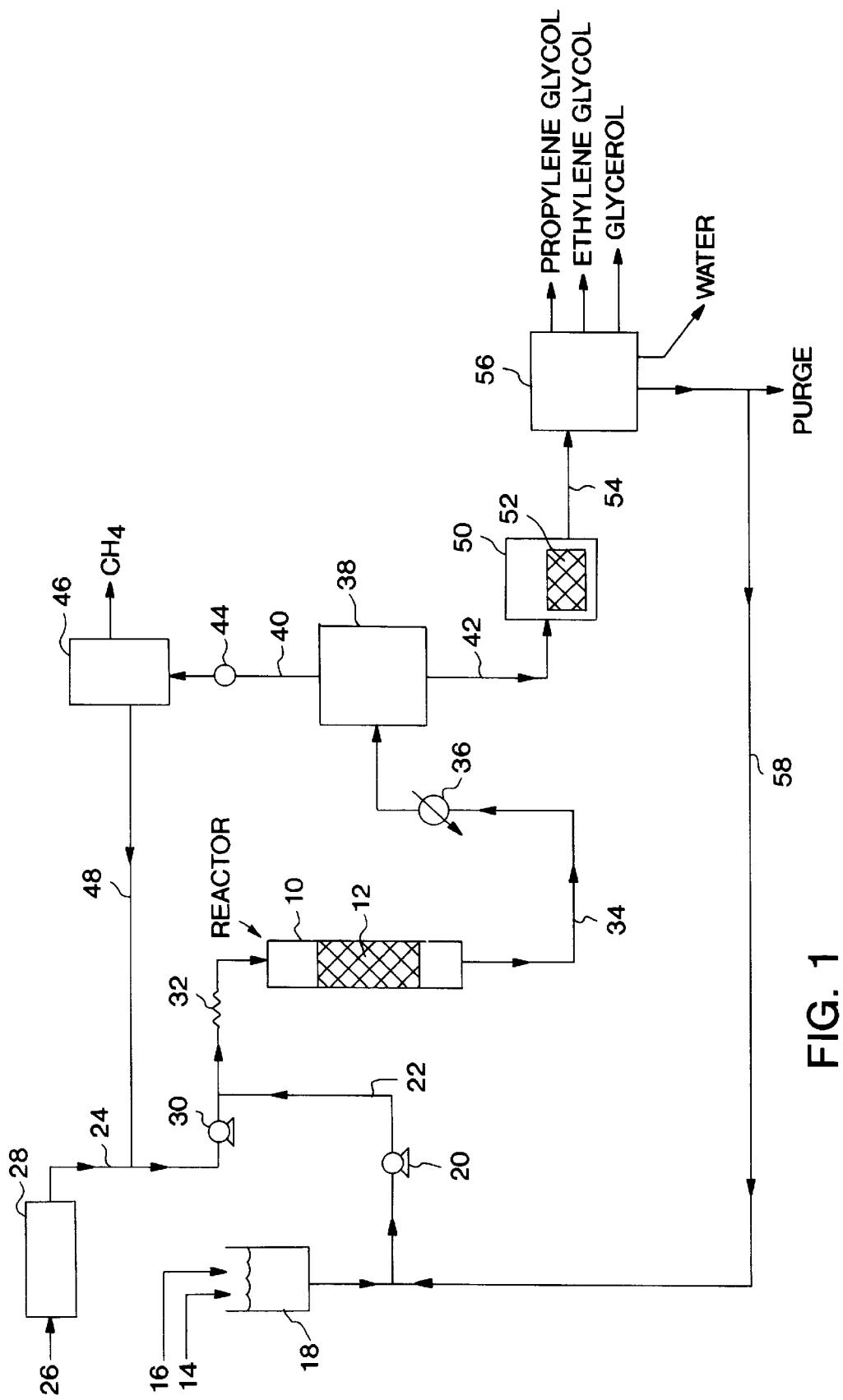
FIG. 1 is a flow diagram for the process for converting sugar alcohol containing feedstocks to polyols.

Sugar alcohols (also known as high molecular weight polyols) are formed by hydrogenation of C5 and C6 sugars such as glucose, xylose, and arabinose which can be derived from corn or other renewable resources. Hydrogenolysis or C—C bond cleavage of these C5 and C6 sugar alcohols gives primarily the lower molecular weight products glycerol, propylene glycol, and ethylene glycol. The reaction also yields by-products such as erythritol and several C4 products such as 1,2-butanediol, 1,3-butanediol, 1,4-butanediol, and 1,2,4-butanediol, which have value in themselves or can be used as substrates in other reaction processes which further convert these by-products to other valuable products. The preferred embodiments of the present invention concern catalysts that catalyze the reaction that converts sugar alcohols or high molecular weight polyols to low molecular weight polyols.

To promote a proper understanding of the present invention, the following terms as they are used herein are hereby defined. The term "MPa" refers to mega-Pascal which is the SI unit of measure for pressure or stress. 1 MPa is equivalent to 1 PSIG×6895.757/$10^6$; or, 1 bar×100,000/$10^6$ or 1 atmosphere (atm)×101,325/$10^6$; or, 1 inches of mercury×3386.388/$10^6$.

The term "dispersion" is defined as the fraction of metal atoms exposed to the gas phase. Conceptually, it is envisioned as the amount of surface area of the metal on the catalyst that is exposed to the reactants. The more spread out the metal, the greater the surface area and, therefore, the greater the dispersion.

The term "selectivity" is defined as the mole of product formed per mole of feed reacted. It is usually presented as a percentage. Selectivity gives an indication of the efficiency of the reaction in producing the desired product.

The term "conversion" is defined as the fractional amount of substrate that is converted into products during the reaction.

The "BET surface area" of the inert supports was calculated according to the method of Brunauer, Emmett, and Teller (BET) disclosed in J. Am. Chem. Soc., 60: 309 (1938).

The term "WHSV" represents the phrase "weight hourly space velocity" which is a measure of the throughput in a flow reactor and as used herein is the kilograms (kg) of sugar alcohol per kg of catalyst per hour.

The present invention provides an improved process that enhances the conversion of sugar alcohols or high molecular weight polyols in a feedstock to low molecular weight polyols of high value such as ethylene glycol, propylene glycol, and glycerol with high selectivity and yield. While the sugar alcohols or high molecular weight polyols can be obtained from a variety of sources, normally they are derived from plants. A key component of the process is the catalyst which in a preferred embodiment comprises ruthenium metal on an activated carbon support that has a high micropore volume so as to facilitate high selectivity to low molecular weight polyols. Preferably, the ruthenium metal has a high dispersion on the support. The method for preparing the catalysts of the present invention, in particular the ruthenium-based catalysts, provides catalysts with performance properties which are superior to the catalysts of the prior art. In particular, as exemplified by the ruthenium on carbon catalysts disclosed herein, the catalysts of the present invention have a remarkable property wherein the metal dispersion on the catalyst actually increases as the conversion reaction proceeds. This increasing dispersion of the metal significantly extends the active life of the catalyst. Thus, the active life of the catalysts of the present invention can last for upwards of 1,000 hours or more in continuous reaction without requiring rehydrogenation of the catalyst and without a significant decrease in product selectivity or yield.

As shown herein for the ruthenium on carbon catalysts of the present invention, the catalyst lasted in a continuous reaction for over 1,000 hours. Unexpectedly, the selectivity and yield of the reaction products increased over the same 1,000 hour time period. Therefore, the catalysts of the present invention are particularly advantageous for use in continuous flow reactor operations because the reactors can be used continuously to make product for significantly long time periods: 40 days or more with the same loading of catalyst without having to interrupt the process to replace the catalyst or rehydrogenate the catalyst. In contrast, the sulfided catalyst which was disclosed by Dubeck in U.S. Pat. No. 4,430,253 would be expected to lose its sulfur over time; therefore, the catalyst's effectiveness would be expected to decrease as the hydrogenolysis reaction proceeded.

The remarkable longevity of the catalyst of the present invention, particularly the ruthenium-based catalysts disclosed herein, is that as the metal dispersion increases during the reaction, the surface area of the metal is increasing which allows increasingly more of the metal to be available for catalyzing the reaction.

To make the catalyst of the present invention, a metal salt in a solvent, preferably water, is deposited on an inert support. After drying to remove the solvent, the metal salt is reduced to its active metal with hydrogen. Afterwards, the catalyst is passivated in an oxygen containing atmosphere which coats the surface of the metal with a layer of an oxide of the metal. The oxidized metal layer enables the catalyst to be maintained without using elaborate storage conditions. Prior to using the catalyst in the process reaction, the catalyst is reduced with hydrogen. The above process for preparing the catalyst appears to impart to the catalyst the remarkable property of increasing metal dispersion on the support during the course of the reaction which in turn extends the longevity of the catalyst in the conversion reaction.

In the conversion reaction, the sugar alcohol feedstock further comprises an alkali promoter material, which is a base, in sufficient quantity to control the pH of the feedstock during the conversion reaction. The base prevents leaching of the metal from the catalyst and enhances the selectivity of the reaction, and the base may have a role in increasing the metal dispersion on the catalysts of the present invention as the conversion reaction proceeds. Promoters for achieving high selectivity in the conversion process of the present invention include alkali metal hydroxides, alkali metal salts, and alkaline earth metal hydroxides, which include, but are not limited to, potassium hydroxide, sodium hydroxide, sodium formate, and sodium carbonate.

In a preferred hydrogenolysis of C5 and C6 sugar alcohols such as xylitol, arabinitol, or sorbitol, the hydrogenolysis is carried out using catalysts of the present invention wherein the catalyst is ruthenium metal supported on an inert support which includes activated or microporous carbon, titania, or alumina. The amount of ruthenium metal deposited on the carbon support can range from about 1.5 to 5.0 wt % with a ruthenium wt % of 2.5 preferred.

Thus, in a preferred embodiment, the catalyst of the present invention comprises ruthenium on activated carbon with a pore size distribution that reflects a high micropore volume. The preferred carbon support for the catalysts of the present invention is a carbon support selected from the group consisting of CTC-95, CTC-120, and PCB which are available from Calgon Carbon Corporation, Pittsburgh, Pa., and CG5P from Cameron-Yakima, Inc., Yakima, Wash. While carbon supports are preferred, other supports such as alumina, silica-alumina, or titania can be used. The method for preparing the preferred catalyst comprises the steps of (1) depositing the ruthenium salt in water on the carbon support, (2) drying to deposit the ruthenium salt onto the carbon surface, (3) reducing the ruthenium salt to the ruthenium metal with hydrogen, and (4) passivating the catalyst with oxygen to produce a layer of ruthenium oxide on surfaces of the ruthenium metal. The oxidation passivates or stabilizes the catalyst and can be achieved by passing a stream of oxygen over the catalyst. Preferably, the oxygen stream comprises about 2% oxygen in an inert gas such as argon. The oxidized catalyst can be stored under atmospheric conditions without a significant loss of catalytic activity. Use of the catalyst requires the step of re-reducing the catalyst with hydrogen prior to the conversion reaction.

Therefore, the present invention provides a catalyst which comprises an essentially pure elemental transition metal on an inert support, wherein the transition metal salt is deposited on the support by drying a water solution of the transition metal salt on the support. Preferably, the transition metal salt on the catalyst is dried at about 25° C. for about 5 hours and then under a vacuum of about 30 inches of mercury at about 100° C. for 12 hours. The transition metal salt is reduced to the elemental transition metal on the support with hydrogen in a process comprising heating the catalyst from 25° C. to 400° C. at a rate of about 0.5° C. per minute under a flow of a gas consisting of 10 volume percent of hydrogen in helium at a rate of about 30 ml per minute; maintaining the catalyst at 400° C. and changing the gas to pure hydrogen; reducing the catalyst in the pure hydrogen for about 16 hours; and cooling the reduced catalyst under a helium flow to room temperature. Then the reduced catalyst is passivated in an oxygen containing atmosphere so as to provide an oxide of the transition metal on surfaces of the transition metal. Preferably, the catalyst is passivated by placing the reduced catalyst in a stream of 2 volume percent of oxygen in an inert gas such as argon at room temperature for about 1 hour. Preferably, the inert support is selected from the group consisting of alumina, titania, and microporous carbon. In a preferred embodiment, the inert support has a BET surface area between about 1 to 1,000 m² per gram. For using the composition in conversion reactions, it is preferable that the transition metal oxide on the surfaces be reduced in a reaction vessel with hydrogen prior to contact with a reaction mixture. In a most preferred embodiment of the catalyst, the transition metal is ruthenium.

The preferred catalyst, in particular the ruthenium on carbon catalyst of the present invention, is effective with a variety of base promoters. In the continuous conversion of sorbitol using a trickle bed reactor, potassium salts such as KOH, and sodium salts such as NaOH, $NA_2CO_3$, and $NaCHO_2$ are preferred. However, the catalyst of the present invention is effective with other promoters such as $Ca(OH)_2$ and MgO. When the promoter is KOH, NaOH, $NA_2CO_3$, or $NaCHO_2$, a preferred concentration of the promoter is 6.8 mM for each wt % of sorbitol. For example, when the sorbitol is 25 wt % the promoter concentration is about 170 mM and when the sorbitol is 35 wt % the promoter concentration is about 240 mM.

In continuous conversion reactions, the ruthenium on carbon catalysts of the present invention are preferred because they were particularly effective at catalyzing conversion of sorbitol to polyols. For example, two Ni-based catalysts, sintered nickel pellets (Metalyst from Degussa, Inc., Ridgefield Park, N.J.) and nickel supported on silica-alumina (from United Catalyst, Inc., Louisville, Ky.) showed poor propylene glycol and glycerol selectivity. However, it was determined that in batch reactions these catalysts can be useful for converting sorbitol to polyols.

FIG. 1 shows a continuous trickle bed process for converting sugar alcohols or high molecular weight polyols to low molecular weight polyols. The process comprises a reactor 10 which is a three-phase reactor commonly run as a trickle bed that contains a fixed bed of catalyst 12. A 20–70% sugar alcohol solution is provided as a water solution at 14. The solution is pH adjusted with an alkali promoter, provided at 16, to maintain the pH of the solution during the reaction to a pH between about 7 to 11. The resulting solution is mixed at 18 and pressurized at 20. The solution feedstream 22 mixed with hydrogen stream 24 before being fed to the reactor 10. Before the hydrogen stream 24 is mixed with the solution feedstream 22, hydrogen at 26 can be passed through a pre-saturator 28 and the resulting hydrogen stream 24 is pressurized by compressor 30. The feedstock stream 22 and hydrogen stream 24 are heated in a preheater 32 to the desired temperature and passed downwardly through the bed in intimate contact with the catalyst 12. Alternatively, the feedstock stream 22 and the hydrogen stream 24 can be passed through the catalyst 12 in a counter-currently wherein the feedstock stream is passed downwardly and the hydrogen stream is passed upwardly, or vice versa.

Thus, in a typical process of the present invention, the catalyst 12 is introduced into the reactor 10 and re-reduced with hydrogen stream 24 without feedstream 22 for about 60 minutes under pressure of about 1.7 MPa (250 PSIG) hydrogen. A total volume of hydrogen equal to 50 bed volumes (volume $H_2$ to bed volume) was passed over the catalyst. Preferably, the catalyst is 2.5% ruthenium on a microporous carbon support. After re-reducing the catalyst 12, the reactor 10 is allowed to cool below 150° C. and vented to low pressure. Then, feedstream 22 containing the sugar alcohol feedstock solution, preferably xylitol, arabinitol, or sorbitol, and a base promoter is introduced in mixture with hydrogen stream 24 into the reactor 10 without opening the reactor. The feedstream rate gives a weight hourly space velocity of about 0.3 to 3.0 kg sugar alcohol solution per kg catalyst per hour. The hydrogen to sugar alcohol feed molar ratio ranges from about 1.4:1 to 8.7:1, with a preferred value of about 4.2:1. The reaction is carried out at a temperature between about 150° C. to 250° C., preferably between 190° C. to 240° C., and the hydrogen pressure is increased to a desired value usually between about 3.4 to 14 MPa (500 to 2,000 PSIG), preferably between about 4.8 to 10.5 MPa (700 to 1,500 PSIG).

After the reaction, the reactor effluent stream 34 is cooled in a heat exchanger 36 against a suitable fluid such as water, and/or other process stream that requires heating, e.g., a process hydrogen stream. The cooled effluent stream is passed through a gas-liquid separator 38, wherein the fluid is separated into an overhead gas stream 40 and a bottom liquid stream 42. The overhead stream 40 contains mainly hydrogen and some methane, and is pressure reduced at 44 and passed to hydrogen purification unit 46. Here the gas is purified to about 90 V % hydrogen and recycled as stream 48 through compressor 30 to reactor 10. Optionally, the gas is purged.

The separator bottom liquid stream 42 is demineralized in a demineralizer 50 containing cationic exchange resins 52 to remove the potassium or sodium ions from the promoter. Then, the demineralized liquid 54 is passed through a separation step 56 wherein ethylene glycol, propylene glycol, and glycerol are purified and recovered. Optionally, after the separation step 40, a portion of the remaining material which comprises C4–C6 alditols, C4–C6 aldoses, alcohols, and polyglycerols are either recycled as stream 58 into the reactor 10, or purged.

For a typical separation for recovering ethylene glycol, propylene glycol, and glycerol (not shown), the demineralized liquid 54 is passed to an alcohol separation column at about atmosphere pressure where the monohydroxyl alcohols are removed. Next, the liquid product is preheated and passed to a low pressure separator from which overhead water vapor is withdrawn. Then, the liquid product is passed through a water distillation column which removes water from the liquid product. The liquid product from the water column is pressure reduced to about 50 to 200 mm Hg pressure and fed to a propylene glycol recovery column to ensure that the temperature at the bottom of the column does not exceed the glycerol decomposition temperature of about 400° C. Propylene glycol of up to about 90 to 99 wt % concentration is recovered with the impurities being mostly diols. After, removal of the propylene glycol, the liquid product is fed to an ethylene glycol recovery column which is also operated at vacuum pressure. The vacuum pressure at the bottom of the column is slightly lower than in the propylene glycol column to prevent the temperature from exceeding the glycerol decomposition temperature. High purity ethylene glycol is recovered and the liquid product is passed to a crude glycerol column to recover remaining traces of diols, triols, and glycerols. In a final distillation step, high purity glycerol is obtained.

While the above describes a process wherein the passivated catalyst is added to the reactor, the present invention also includes the above process except that the catalyst is made in the reactor that the conversion reaction will take place. In this manner the entire process from catalyst preparation to the conversion reaction is performed in the same vessel.

The following examples are intended to promote a further understanding of the present invention.

EXAMPLE 1

This example illustrates the preparation of several of the catalysts of the present invention, including the preferred 2.5% Ru on CTC-120 catalyst. The carbon supports used were available from Calgon Carbon Corporation, Pittsburgh, Pa.

In general, for making the catalysts, the loading of the ruthenium varied between 1.5% and 5% ruthenium. In addition, mixed metal catalysts were prepared using ruthenium and rhenium as the active metals. Following preparation, each catalyst was evaluated using hydrogen chemisorption to determine the dispersion of the ruthenium. This example illustrates the preparation of three ruthenium catalysts which varied in the amount of ruthenium loaded and two composite catalysts comprising ruthenium/rhenium.

To make a 1.5% Ruthenium on CTC-120 catalyst, a solution was made consisting of 0.192 gram of $RuCl_3xH_2O$ dissolved in 4.25 ml of deionized water. This solution was deposited onto 5 gram of CTC-120 (CALGON Carbon CTC support) in 1 to 2 ml aliquots. Each aliquot was allowed to absorb into the carbon. Afterwards, the carbon was continuously rolled for 5 minutes. After the final addition and rolling, the carbon was dried in a vacuum oven at 100° C. for 12 hours under reduced pressure to form the catalyst. The dried catalyst was placed in a tube furnace, purged with argon, and then reduced by exposure to pure hydrogen. The reduction process started at 120° C.; the temperature was ramped from 120° to 400° C. at 0.5° C. per minute and then held at 400° C. for 9 hours. Following reduction, the catalyst was passivated for 1 hour in 2% oxygen in argon. The catalyst developed an oxidized metal layer on the surface which passivated (stabilized) the catalyst.

To make the preferred 2.5% Ruthenium on CTC-120 catalyst, a solution was made consisting of 0.319 gram of $RuCl_3xH_2O$ dissolved in 4.25 ml of deionized water. This solution was deposited onto 5 gram of CTC-120 (CALGON Carbon CTC support) in 1 to 2 ml aliquots. Each aliquot was allowed to absorb into the carbon. Afterwards, the carbon was continuously rolled for 5 minutes. After the final addition and rolling, the carbon was dried in a vacuum oven at 100° C. for 12 hours under reduced pressure to form the catalyst. The dried catalyst was placed in a tube furnace, purged with argon, and then reduced by exposure to pure hydrogen. The reduction process started at 120° C.; the temperature was ramped from 120° to 400° C. at 0.5° C. per minute and then held at 400° C. for 9 hours. Following reduction, the catalyst was passivated for 1 hour in 2% oxygen in argon. The catalyst developed an oxidized metal layer on the surface which passivated the catalyst.

To make a 5.0% Ruthenium on CTC-120 catalyst, a solution was made consisting of 0.639 gram of $RuCl_3xH_2O$ dissolved in 4.25 ml of deionized water. This solution was deposited onto 5 gram of CTC-120 (CALGON Carbon CTC support) in 1 to 2 ml aliquots. Each aliquot was allowed to absorb into the carbon. Afterwards, the carbon was continuously rolled for 5 minutes. After the final addition and rolling, the carbon was dried in a vacuum oven at 100° C. for 12 hours under reduced pressure to form the catalyst. The dried catalyst was placed in a tube furnace, purged with argon, and then reduced by exposure to pure hydrogen. The reduction process started at 120° C.; the temperature was ramped from 120° to 400° C. at 0.5° C. per minute and then held at 400° C. for 9 hours. Following reduction, the catalyst was passivated for 1 hour in 2% oxygen in argon. The catalyst developed an oxidized metal layer on the surface which passivated the catalyst.

To make a 1.5% Ruthenium/1.5% Rhenium on CTC-120 catalyst, a solution was made consisting of 0.191 gram of $RuCl_3xH_2O$ and 0.142 gram perrhenic acid dissolved in 4.25 ml of deionized water. This solution was deposited onto 5 gram of CTC-120 (CALGON Carbon CTC support) in 1 to 2 ml aliquots. Each aliquot was allowed to absorb into the carbon. Afterwards, the carbon was continuously rolled for 5 minutes. After the final addition and rolling, the carbon was dried in a vacuum oven at 100° C. for 12 hours under reduced pressure to form the catalyst. The dried catalyst was placed in a tube furnace, purged with argon, and then reduced by exposure to pure hydrogen. The reduction process started at 120° C.; the temperature was ramped from 120° to 400° C. at 0.5° C. per minute and then held at 400° C. for 9 hours. Following reduction, the catalyst was passivated for 1 hour in 2% oxygen in argon. The catalyst developed an oxidized metal layer on the surface which passivated the catalyst.

To make a 2.5% Ruthenium/2.5% Rhenium on CTC-120 catalyst, a solution was made consisting of 0.318 gram of $RuCl_3xH_2O$ and 0.237 gram perrhenic acid dissolved in 4.25 ml of deionized water. This solution was deposited onto 5 gram of CTC-120 (CALGON Carbon CTC support) in 1 to 2 ml aliquots. Each aliquot was allowed to absorb into the carbon. Afterwards, the carbon was continuously rolled for 5 minutes. After the final addition and rolling, the carbon was dried in a vacuum oven at 100° C. for 12 hours under reduced pressure to form the catalyst. The dried catalyst was placed in a tube furnace, purged with argon, and then reduced by exposure to pure hydrogen. The reduction process started at 120° C.; the temperature was ramped from 120° to 400° C. at 0.5° C. per minute and then held at 400° C. for 9 hours. Following reduction, the catalyst was passivated for 1 hour in 2% oxygen in argon. The catalyst developed an oxidized metal layer on the surface which passivated the catalyst.

The catalysts were stored in an oxidized state. Prior to using any of the above catalysts in a conversion reaction, the catalyst was activated by reducing in hydrogen. It will be readily apparent to one skilled in the art that larger quantities of the above catalysts can be prepared by the above process by scaling the quantities of reagents to any desired levels.

that larger quantities of the above catalysts can be prepared by the above process by scaling the quantities of reagents to any desired levels.

TABLE 1

| # | Catalyst ID | Metal load (%) | Support | BET surface area (m$^2$/g) | Support size (mesh) | Dispersion (%) | Precursor |
|---|---|---|---|---|---|---|---|
| 1 | CG5P-A | 5.4 | CG5P carbon | 648 | −200 | 10 | RuCl$_3$x H$_2$O in water |
| 2 | SA135-C | 5 | Silica alumina 135 | 440 | −100 | 14 | RuCl$_3$x H$_2$O in water |
| 3 | SG6-D | 4.4 | SG6 carbon | 777 | −100 | 10 | RuCl$_3$x H$_2$O in water |
| 4 | ALG-E | 4.7 | γ-Al$_2$O$_3$ | 45 | +100 | 13.5 | RuCl$_3$x H$_2$O in water |
| 5 | CG6M-F | 5 | CG6M carbon | 728 | −100 +200 | 13 | RuCl$_3$x H$_2$O in water |
| 6 | CG5P-G | 5 | CG5P carbon | 648 | −200 | 6 | RuCl$_3$x H$_2$O in water |
| 7 | CG5P-H | 5 | CG5P carbon | 648 | −200 | 3 | RuCl$_3$x H$_2$O in EtOH |
| 8 | CG5P-NO1-I | 5 | CG5P carbon | 648 | −200 | 38 | Ru(NO)NO$_3$ in water |
| 9 | TiP25-CL9-J | 5 |  | 49 | −200 | — | RuCl$_3$x H$_2$O in water |

EXAMPLE 2

This example illustrates the preparation of several additional ruthenium-based catalysts made on supports consisting of activated carbon.

To make catalyst CG5P-A (5.4% ruthenium on carbon, 50 gram of activated carbon (#CG5P, 200 mesh, N$_2$ BET surface area of 648 m$^2$ per gram from Cameron-Yakima, Inc., Yakima, Wash.) was placed in an aqueous solution of RuCl$_3$xH$_2$O (Aldrich Chemical Co., Milwaukee, Wis.). Excess solution was present such that the resulting mixture was a slurry. The resulting slurry was placed in a rotating evaporator and slowly dried under a vacuum (50 to 85 kPa at 60 to 80° C.) for 2 hours. When dried, the dried material was transferred to a quartz tube furnace and purged with argon. Hydrogen was then passed over the material at 1 atmosphere and at 30 ml per minute to reduce the chloride salt to ruthenium metal. Then the temperature was ramped from 25° C. to 400° C. at a rate of 2° C. per minute. The material was held at 400° C. for 16 hours. The resulting catalyst was purged in argon, cooled to room temperature and then passivated by oxidizing the surface of the ruthenium metal in a stream of 2% oxygen in argon for 1 hour.

To make catalyst SG6-D (4.4% ruthenium on carbon), 10 gram of activated carbon (#CG5P, -100 mesh, N$_2$BET surface area of 777 m$^2$ per gram from Cameron-Yakima, Inc.) was dried overnight at 100° C. and a vacuum of 30 inches of Hg to remove all trapped water. The precursor solution of RuCl$_3$xH$_2$O (from Aldrich Chemical Co.), made up in a volume that was previously determined to just fill the pore volume of the carbon, i.e., incipient wetness, was added in small increments to the carbon while stirring with a spatula. After addition of all the precursor solution, the wetted (impregnated) carbon was placed in a rotary evaporator and dried under a vacuum of 30 inches of Hg for 16 hours at room temperature. Then the impregnated carbon was heated to 50° C. for 4 hours to complete the drying. Afterwards, the impregnated carbon was heated in argon to 120° C. in a quartz tube furnace. Hydrogen was then passed over the impregnated carbon at 30 ml per minute and the temperature was ramped from 120° C. to 400° C. at 0.5° C. per minute. Then the impregnated carbon was held at 400° C. for 9 hours. Finally, the catalyst was purged with argon, cooled to room temperature, and passivated by oxidizing the surface of the ruthenium metal in a stream of 2% oxygen in argon for 1 hour.

Table 1 shows the above catalysts and several other catalysts of the present invention. Prior to using the passivated catalysts, the catalysts were activated by reducing in hydrogen. It will be readily apparent to one skilled in the art

EXAMPLE 3

BET surface area, micropore volume, and ruthenium dispersion of the 2.5% Ru on CTC-95, 2.5% Ru on CTC-120, and 2.5% Ru on PCB catalysts were evaluated. In particular, the metal dispersion on the catalysts was measured before and after subjecting the catalysts to reaction conditions.

The three above catalysts were prepared according to the methods shown in Examples 1 and 2. All three catalysts contained 2.5% by weight ruthenium. The total surface area of the supports was evaluated by nitrogen adsorption at 77 K according to the method of Brunauer, Emmett, and Teller (BET), pore volumes were measured by nitrogen adsorption up to a relative pressure (P/P$_o$) of 0.95, and metal dispersion was determined by chemisorption of hydrogen on the metal under carefully controlled conditions of temperature and gas composition. The ruthenium dispersion of the catalysts was measured both before converting sorbitol to polyols and then again after the conversion reaction. To minimize possible interferences with the measurements, both before and after the reaction the catalysts were reduced at 400° C., so that any hydrogen desorption from the carbon surface would be same for both catalysts. This precaution minimized any potential for false measurements due to hydrogen desorption. The catalyst dispersion results from these reactions are shown in Table 2.

The results demonstrate a novel and unexpected property of the catalysts. The ruthenium dispersion, which is the fraction of ruthenium atoms exposed to the gas phase, increased greatly following exposure to reaction conditions. This result was unexpected, as generally catalyst metal motility is limited at temperatures below 600–700 K. Furthermore, in general, when a metal becomes mobile it tends to sinter, which reduces dispersion. This property of increased dispersion as the reaction proceeds has not been described in the prior art.

The enhanced ruthenium dispersion during the reaction may also have been affected by the KOH promoter which was used in the reaction. The promoter may have enhanced dispersion or enhanced hydrogen uptake by the ruthenium, or both. Or, the combination of water, hydrogen, and perhaps the promoter may have contributed to the increased dispersion of the ruthenium on the catalyst as the reaction proceeded. However, regardless of the mechanism for the increased dispersion, the results indicate that catalysts prepared and used according to the present invention will remain activated over time via development of increased metal dispersion. As shown in Example 14, the increased dispersion was manifested by an increased sorbitol conversion and increased propylene glycol yield over time.

TABLE 2

Properties of 2.5 wt % Ru on different Carbon Supports

| Carbon Support (catalyst ID) | BET surface area (m$^2$/g) | Micropore volume (cc/g) | Total pore volume (cc/g) | % Ru dispersion before rxn | % Ru dispersion after rxn |
|---|---|---|---|---|---|
| Calgon CTC-120 (55794-96) | 1480 | 0.75 | 0.85 | 9.5 | 28 |
| Calgon PCB (557494-130) | 950 | 0.51 | 0.55 | 3 | 26 |
| Englehard CT-95 (55794-131 | 1240 | 0.65 | 0.71 | 3 | 23 |

EXAMPLE 4

This example illustrates the procedure for performing batch reactions for preparing low molecular weight polyols from xylitol feedstock using the catalysts of the present invention.

The batch reactions for catalyst screening and initial kinetic analyses were carried out in a 300 ml capacity Parr Autoclave (Parr Instrument Co., Joliet, Ill.) equipped with a special gas entraining impeller and a temperature controller that controls the temperature of the reactor within ±1° C. The reactor bomb was made of 316 stainless steel with a maximum rated tI pressure of 3,000 psi at a maximum temperature of 350° C. The reactor included a device for collecting liquid samples over the course of the experiment and contained a gas outlet to conduct gas analysis as the reaction progressed.

Several feedstock materials were used in the reaction studies. First, reagent-grade sugar alcohols were purchased and used in the catalyst screening. Xylitol (98%, from Aldrich Chemical Co.) and arabinitol (98%, from Aldrich Chemical Co.) were used. Commercial grade sorbitol from a corn wet mill was used to evaluate the process with C6 sugars. For several reaction studies, corn fiber hydrolysate obtained from a wet mill (Grain Products Corporation, Muscatine, Iowa) was used as a feedstock. This material contained approximately equal quantities of xylose and arabinose, and a small quantity of glucose. All feedstocks were run at concentrations ranging from 25% to 70% by weight in aqueous solution. Water used in these studies was HPLC grade water (from J.T. Baker, Pillipsburg, N.J.). promoters were obtained as solids or solutions from several vendors. Ultra-high purity hydrogen gas (99.999% hydrogen, from AGA Gas Co., Lansing, Mich.) was used in all runs.

To conduct a reaction, catalyst was first introduced into the reactor and re-reduced at 200° C. and 1.7 MPa (250 PSIG) hydrogen at a flow rate of 100 sccm/min for 60 minutes (which is equivalent to 50-bed volumes). After cooling the reactor below 150° C. and venting to low pressure, feed solution was introduced without opening the reactor. The reactor was then heated to the desired reaction temperature and hydrogen pressure was increased to the desired value. Liquid samples were periodically removed for evaluation during the course of the reaction. The reaction lasted from 2 to 8 hours, with 4 to 6 hours the most typical reaction time. After most reactions, only a final gas analysis was performed.

The liquid product mixtures from the reactions were analyzed using high pressure liquid chromatography (HPLC) system consisting of an HPLC pump, a UV detector, and an RI detector. Software was used to control the entire HPLC system and process data obtained from the system. An Aminex 87H HPLC column (Bio-Rad Laboratories, Irvine, Calif.) at a temperature of 65° C. was used for the separation of the compounds. A solution of 5 mM sulfuric acid in water was used as the mobile phase at a flow rate of 0.45 ml/minute. Ethanol was used as an internal standard. The filtered samples were diluted 25 times and mixed with an equal amount of 10 gram per liter aqueous ethanol solution and injected into the column. Lactic acid concentration was calculated using a UV detector at a wavelength at 214 nm. The concentrations for the rest of the compounds were calculated using the RI detector. A typical analysis run time was 40 minutes.

EXAMPLE 5

This example illustrates the procedure for performing trickle-bed or continuous conversion reactions for preparing low molecular weight polyols from sugar alcohol feedstock using various catalysts of the present invention.

Continuous hydrogenolysis reactions were carried out in a fixed-bed, three-phase reactor run in the trickle-bed mode. The reactors used generally had the following design. The reactor (0.62 inch inner diameter (ID) and 18 inches in length) was charged with 50 to 75 ml catalyst. The reactor was jacketed and the temperature was controlled with temperature controllers (Omega Engineering, Stanford, Conn.). The feed gas rate to the reactor was controlled by mass flow controllers. Feed hydrogen was passed through water saturators prior to entering the reaction to avoid flashing of the liquid feed in the reactor. The liquid solution was fed to the reactor via an HPLC pump. Reactor effluent was passed through a cold-water condenser and into a phase separator where the liquid product was allowed to settle out. Gas effluent was passed through a back pressure regulator to the exhaust. A portion of the gas effluent was drawn into a mass spectrometer where effluent gas composition was determined.

Reactions were carried out at temperatures from 190° C. to 250° C. and at pressures from 3.4 to 10.3 MPa (500 to 1,500 PSIG). The sugar alcohol (prepared as in Example 4) was fed to the reactor in aqueous solutions of 25% to 70% by weight. The liquid feed rate to the reactor ranged from 0.5 to 4.0 ml per minute, which gave a weight hourly space velocity of 0.3 to 3 kg sugar per kg catalyst per hour. The hydrogen to sugar alcohol feed molar ratio ranged from 1.4:1 to 8.7:1, with a preferred value of 4.2:1.

In the trickle bed reaction, the catalyst was first loaded into the reactor and then reduced under the same conditions as noted above in Example 4. Once the reduction reaction was completed, water was fed to the reactor while the reactor temperature was brought to the desired steady-state condition. The liquid was then switched to a sugar alcohol solution and hydrogen pressure was increased to the desired value. Typically, it took 90 to 120 minutes for steady-state product compositions to be achieved at any particular set of reaction conditions. Analysis of the liquid samples were performed as shown in Example 4.

EXAMPLE 6

Several catalysts shown in Table 2 were evaluated for effectiveness in batch reactors for the conversion of xylitol to ethylene glycol (EG), propylene glycol (PG), and glycerol (Gly) in batch reactors. These prepared catalysts were also compared to several of the commercially available catalysts shown in Table 3.

TABLE 3

| # | Catalyst ID/source | Metal/Support | Run ID | Support size, mesh | Dispersion |
|---|---|---|---|---|---|
| 1 | 12046/PMC | 5% Ru/C | 0721 | −325 | ~34 |
| 2 | ESCAT440/Engelhard | 5% Ru/C | 1020A | — | — |
| 3 | H7702X/D/Degussa | 3% Ru/TiO$_2$ | 0922A | — | ~40 |
| 4 | H101BB/W/Degussa | 5% Ru/C | 0923A | — | 14% |
| 5 | H214XR/W/Degussa | 5% Ru/Al$_2$O$_3$ | 0924A | — | — |
| 6 | 5222/Press. Chem. | 60% Ni/Al$_2$O$_3$ | 1023A | — | — |

PMC is Precious Metals Corporation, Sevierville, Tennessee; and, Press. Chem is Pressure Chemical Company, Pittsburgh, Pennsylvania.

The reactor conditions were at 230° C. at 9 MPa (1350 PSIG) for 4 hours. The promoter for the reactions was 0.17 M KOH (1 wt % in solution) and the catalysts were added in the amount of 1 gram per 100 gram of solution.

Figure 2:
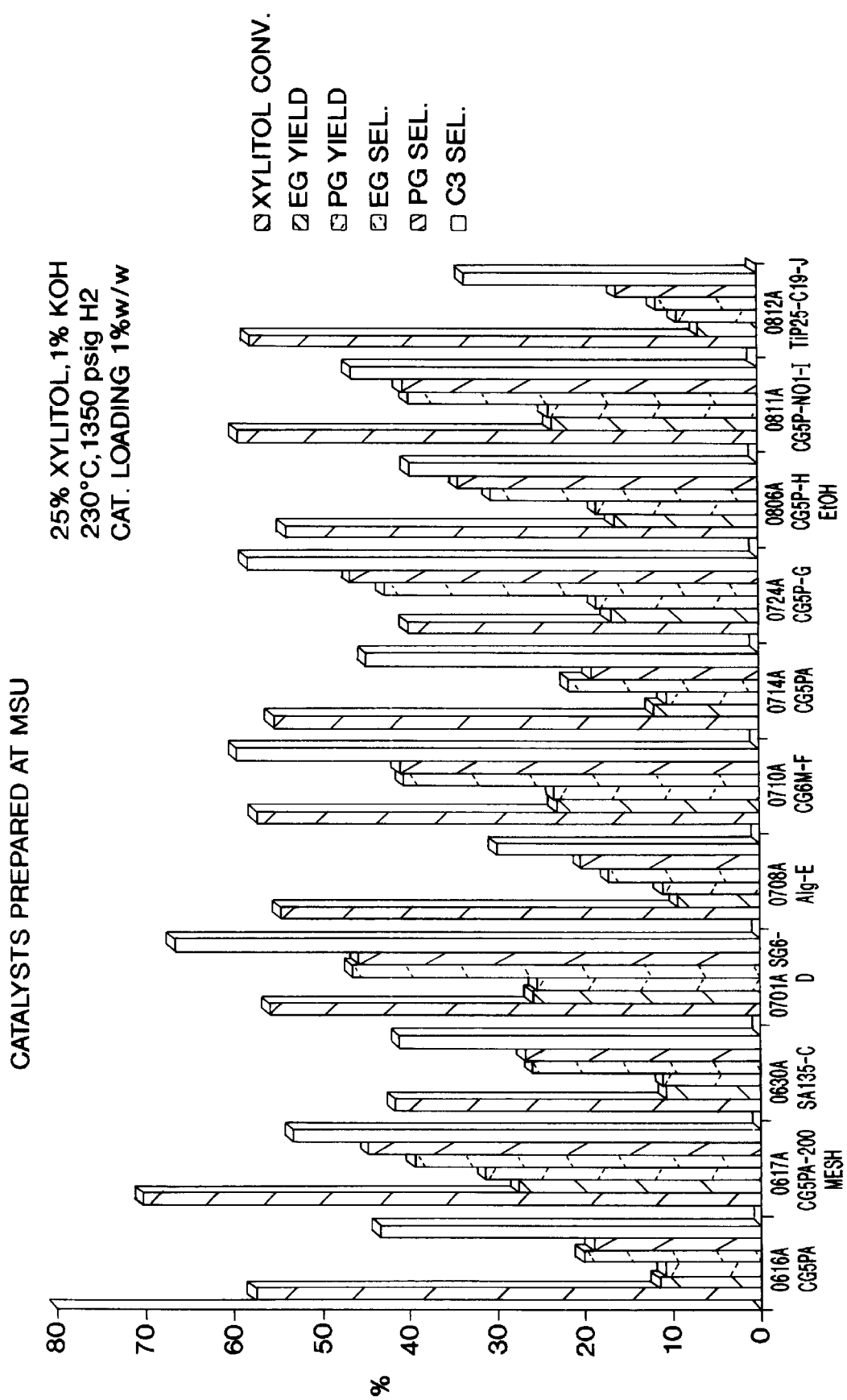
FIG. 2 shows the percent xylitol conversion in hydrogenolysis reactions catalyzed by several prepared catalysts.

The results for the prepared catalysts are summarized in FIG. 2. Detailed results of the yield and selectivity for two of the catalysts, CG5P-A and SG6-D, are shown in Table 4. The results show that the microporous carbon supports of the present invention exhibited high selectivity ethylene glycol and propylene glycol.

Figure 3:
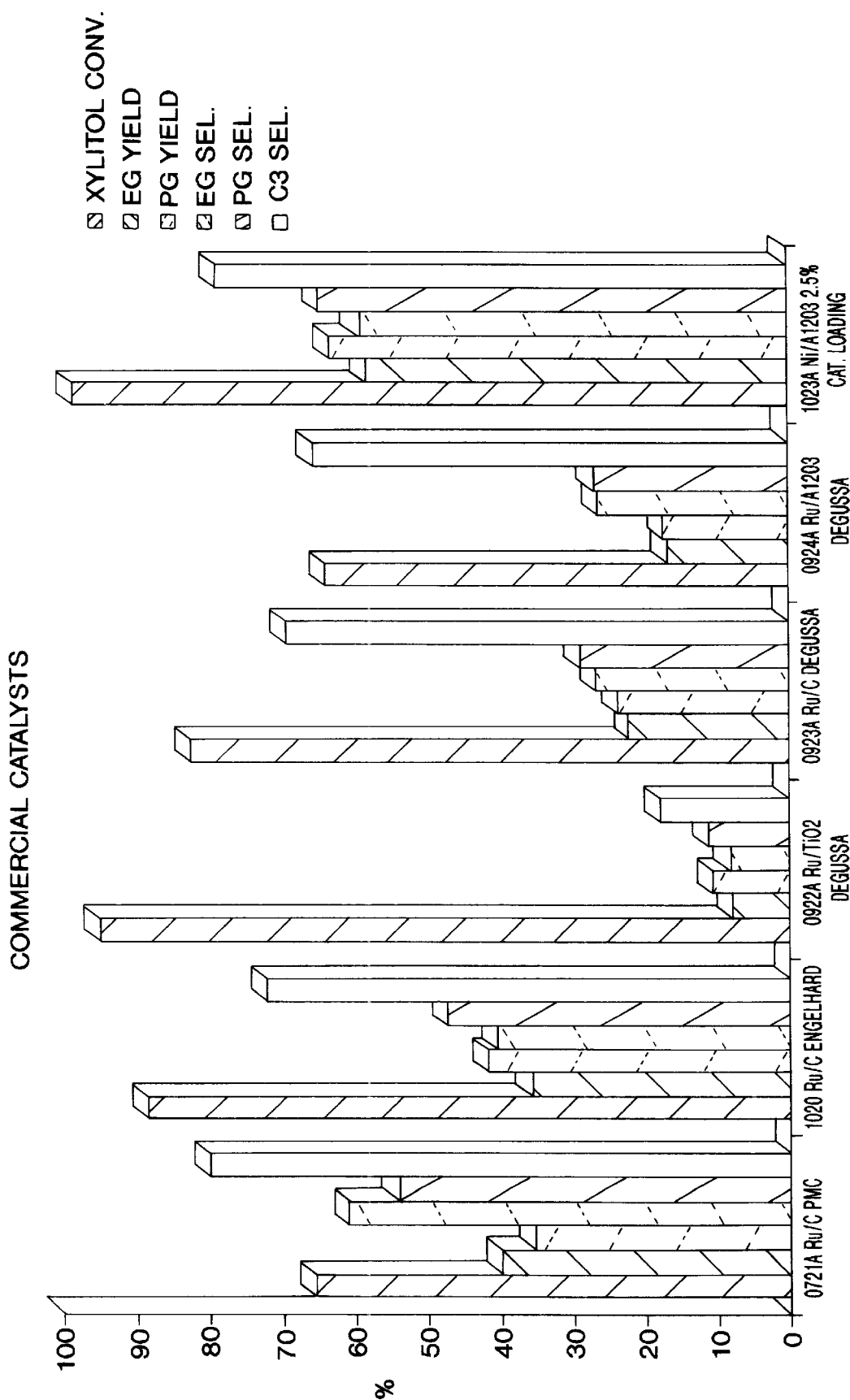
FIG. 3 shows percent xylitol conversion in hydrogenolysis reactions catalyzed by several commercial catalysts.

The results for the commercial catalysts are also summarized in FIG. 3 with detailed results for two of the catalysts, 5% Ru/C, PMC, Inc. and 60% Ni/Al$_2$O$_3$, shown in Table 4. Both of these commercial catalysts exhibited high selectivity towards ethylene glycol, and propylene glycol. In contrast, the palladium, copper chromate, and Raney Nickel catalysts showed little or no activity toward the conversion of xylitol to ethylene glycol, propylene glycol, and glycerol. The batch reactor results demonstrate that C5 sugar alcohols can be converted efficiently to polyol products over ruthenium and several other metal catalysts; however, the microporous carbon supports are preferred.

EXAMPLE 7

The ability of the 2.5% Ru on CTC-120 catalyst to affect efficient hydrogenolysis of xylitol in a continuous, steady-state conversion of xylitol to low molecular weight polyols was evaluated.

The catalyst was prepared as shown in Example 1 and the trickle bed process of Example 5 was performed under a variety of temperatures and feed flow rates as noted in Table 5. For each of the reactions, the pressure was 8 MPa (1,200 PSIG), the hydrogen to feed molar ratio was 5.1 to 1, the promoter concentration was 0.17 M KOH, the WHSV ranged from 0.8 to 1.2 kg per kg catalyst per hour, and the xylitol feed was provided as a solution containing 25% xylitol.

The results in Table 5 show that using the 2.5% Ru on CTC-120 catalyst, the reaction had a propylene glycol selectivity that was 70.1% and a ethylene glycol selectivity that was 68.1% (Table 5, experiment 90202T-S6) at a xylitol feed conversion of less than 56%. Overall selectivity for the desired C2–C3 bond cleavage in xylitol exceeded 90% under these conditions. This result is an improvement over the prior art. There was no significant difference in propylene glycol or ethylene glycol selectivity within the 231° to 244° C. temperature range or in the 0.40 to 1.20 WHSV range. Therefore, the results show that the 2.5% Ru on CTC-120 catalyst achieved high conversion and high yield

TABLE 4

| | | Reaction Parameters | | | | |
|---|---|---|---|---|---|---|
| Experiment[1] | Catalyst descript. | Feed Comp. | Catalyst charge (g/g feed sol'n) | Pressure (psi) | Temp. (° C.) | Promoter Conc. |
| 0617A | 5 wt % Ru CG5P-A carbon | 25 wt % xylitol | 0.01 | 1350 | 230 | 0.17 M KOH |
| 0701A | 5 wt % Ru SG6-D carbon | 25 wt % xylitol | 0.01 | 1350 | 230 | 0.17 M KOH |
| 0721A | 5 wt % Ru (PMC, Inc.) | 25 wt % xylitol | 0.01 | 1350 | 230 | 0.17 M KOH |
| 1023A | 60 wt % Ni γ-Al$_2$O$_3$ | 25 wt % xylitol | 0.025 | 1350 | 230 | 0.17 M KOH |

| | Feed Conversion and Product Selectivity | | | |
|---|---|---|---|---|
| Experiment | Feed conversion | PG | EG | Glycerol | Lactic acid |
| 0617A | 53.2 | 49.2 | 46.6 | 8.4 | 6.0 |
| 0701A | 37.5 | 43.3 | 47.4 | 6.9 | 16.2 |
| 0721A | 65.6 | 54.3 | 60.9 | 14.8 | 10.8 |
| 1023A | 97.7 | 64.1 | 58.9 | 7.6 | 6.4 |

[1]Batch reactions in autoclave. Reaction time 4 hr.

of ethylene glycol, propylene glycol, and glycerol from xylitol in a continuous reactor, and that the catalyst maintained its activity under a wide range of process conditions. The results further showed that the 2.5% Ru on CTC-120 catalyst is preferred for the conversion of C5 sugar alcohols to low molecular weight polyols.

ethylene glycol, and glycerol was significantly better under similar conditions for the 2.5% Ru on CTC-120 and 2.5% Ru on PCB catalysts than for the 2.5% Ru on CTC-95 catalyst. Thus, the 2.5% Ru on CTC-120 and 2.5% Ru on PCB catalysts are preferred for the continuous conversion of sorbitol to low molecular weight polyols.

TABLE 5

| | | | Reaction Parameters | | | | |
|---|---|---|---|---|---|---|---|
| Experiment | Catalyst descript. | Feed Comp. | WHSV (kg/kg cat/hr) | $H_2$:Feed molar ratio | Pressure (psi) | Temp. (° C.) | Promoter Conc. |
| 90129T-S6 | 2.5 wt % | 25 wt % xylitol | 0.80 | 5.1 | 1200 | 231 | 0.17 M KOH |
| 90129T-S3 | Ru/CTC-120 | 25 wt % xylitol | 0.80 | 5.1 | 1200 | 244 | 0.17 M KOH |
| 90129T-S9 | carbon | 25 wt % xylitol | 0.80 | 5.1 | 1200 | 258 | 0.17 M KOH |
| 90202T-S9 | | 25 wt % xylitol | 0.40 | 5.1 | 1200 | 231 | 0.17 M KOH |
| 90202T-S6 | | 25 wt % xylitol | 0.60 | 5.1 | 1200 | 231 | 0.17 M KOH |
| 90202T-S2 | | 25 wt % xylitol | 1.20 | 5.1 | 1200 | 231 | 0.17 M KOH |

| | Feed Conversion and Product Selectivity | | | | | |
|---|---|---|---|---|---|---|
| Experiment | Feed conversion | PG | EG | Glycerol | $C_4$ | Lactic acid | Methane |
| 90129T-S6 | 55.8 | 70.1 | 68.1 | 13.2 | 1.7 | 2.3 | 19.3 |
| 90129T-S3 | 67.3 | 65.6 | 57.3 | 8.1 | 3.7 | 1.8 | 18.3 |
| 90129T-S9 | 72.0 | 6.7 | 55.3 | 6.5 | 3.5 | 2.2 | 21.2 |
| 90202T-S9 | 79.0 | 67.1 | 59.5 | 12.2 | 5.0 | 2.0 | 5.8 |
| 90202T-S6 | 66.3 | 70.8 | 66.7 | 12.6 | 4.3 | 2.1 | 6.2 |
| 90202T-S2 | 44.7 | 71.1 | 74.9 | 16.5 | 3.1 | 2.5 | 7.4 |

C4 products are compound such as 1,2-butanediol, 1,3-butanediol, 1,4-butanediol, and 1,2,4-butanediol.

EXAMPLE 8

The efficacy of catalysts consisting of ruthenium deposited on the CTC-95, CTC-120, or PCB carbon supports were evaluated in a trickle bed reactor.

The trickle bed reaction conditions were similar to the conditions provided in Example 5 with the following specific parameters. The sugar alcohol feedstock composition was 25 wt % sorbitol, the hydrogen to feedstock molar ratio was 5 to 1, the pressure was 8.3 MPa (1,200 PSIG), and the promoter was 0.17 M KOH. For the 2.5 wt % Ru on CTC-95 catalyst, the WHSV (kg per kg catalyst per hour) was 0.75, and the temperature was 220° or 230° C. For the 2.5 wt % Ru on PCB catalyst, the WHSV was 0.73, and the temperature was 220° C. For the 2.5 wt % Ru on CTC-120 catalyst, the WHSV was 0.8, and the temperature was 217° C. The results are shown in Table 6.

The continuous conversion of sorbitol to the desired polyol products was particularly efficient using the 2.5% Ru on CTC-120 and 2.5% Ru on PCB carbon catalysts. As summarized in Table 6, the selectivity to propylene glycol, The sorbitol conversion to low molecular weight polyols and other useful products was very high on the 2.5% Ru on CTC-120 catalyst. However, it should be noted that selectivity decreased with increasing temperature (data not shown). This is because as the temperature was increased, secondary reactions became increasing favored which skewed the production towards the secondary reaction products and away from the desired ethylene glycol, polyethylene glycol, and glycerol products. Similar results showing reduced selectivity with increased temperature would be expected with any other catalyst as well.

As was shown in Table 2 of Example 3, both the 2.5% Ru on CTC-120 and 2.5% Ru on PCB catalysts had a higher dispersion increase over time during the reaction than the 2.5% Ru on CTC-95 catalyst. This remarkable observation was unexpected since it had been expected that catalyst efficacy would be related to pore size of the support. However, as this example shows, the performance of the catalysts of the present invention is related to dispersion of the metal on the support. No correlation between catalyst efficacy and support pore size or pore volume was observed.

TABLE 6

| | | | Reaction Parameters | | | | |
|---|---|---|---|---|---|---|---|
| Experiment | Catalyst description | Feed Comp. | WHSV (kg/kg cat/hr) | $H_2$:Feed molar ratio | Pressure (psi) | Temp. (° C.) | Promoter Conc. |
| 90914T-S3 | 2.5 wt % Ru/ CTC-95 carbon | 25 wt % sorbitol | 0.75 | 5.1 | 1200 | 220 | 0.17 M KOH |
| 90909T-S3 | 2.5 wt % Ru/ PCB carbon | 25 wt % sorbitol | 0.73 | 5.1 | 1200 | 220 | 0.17 M KOH |
| 90303T-S9 | 2.5 wt % Ru/ CTC-120 carbon | 25 wt % sorbitol | 0.8 | 5.1 | 1200 | 217 | 0.17 M KOH |

TABLE 6-continued

| | Feed Conversion and Product Selectivities | | | | | | | |
|---|---|---|---|---|---|---|---|---|
| Experiment | Feed conversion | PG | EG | Glycerol | $C_4$ | $C_5$ | Lactic acid | Methane |
| 90914T-S3 | 85.6 | 50.2 | 25.4 | 24.9 | 16.4 | 4.8 | 5.0 | 29.0 |
| 90909T-S3 | 70.4 | 67.7 | 42.4 | 44.6 | 21.5 | 5.1 | 5.2 | 12.2 |
| 90303T-S9 | 63.2 | 75.6 | 51.9 | 40.6 | 15.5 | 0 | 3.3 | 5.1 |

Selectivity is defined as (mole produce formed/mole feed reacted) × 100. The theoretical maximum selectivity for PG and glycerol from sobitol is 200. C4 products are compounds such as 1,2-butanediol, 1,3-butanediol, 1,4-butanediol, and 1,2,4-butanediol.

EXAMPLE 9

To determine whether the concentration of sorbitol feedstock had an effect on the performance of the 2.5% Ru on CTC-120 catalyst, a series of reactions were performed under several concentrations of sorbitol.

The reactions were conducted in a trickle bed reactor under conditions similar to those in Example 5 with the following specific conditions. The WHSV was 0.54 per hour, the hydrogen to feedstock molar ratio was 5 to 1, pressure of 8.3 MPa (1,200 PSIG), and the temperature was 220° C. The feedstock sorbitol concentrations were 25, 35, 50, and 70 wt % with KOH promoter concentrations of 0.17 M, 0.24 M. 0.34 M, and 0.48 M, respectively.

Table 7 shows that the 2.5% Ru on CTC-120 catalyst is effective over a sorbitol feed concentration range between at least 25% to 70%. In particular, the catalyst was effective without any significant deviation in performance between 25 to 50 wt % sorbitol in solution. In fact, the catalyst performed reasonably well at a sorbitol concentration as high as 70 wt %.

EXAMPLE 10

The product yields and sorbitol conversion over the 2.5% Ru on CTC-120 catalyst using KOH, NaOH, $Na_2CO_3$, HCOONa, $Ca(OH)_2$, or MgO as the reaction promoter were evaluated.

The conditions for each of the reactions were similar to the conditions in Example 5 with the following specific parameters. The feedstock sorbitol composition was 25 wt %, the WHSV was 0.80, the hydrogen to feedstock molar ratio was 5 to 1, the pressure was 8.3 MPa (1,200 PSIG), and the temperature was 220° C. The promoter concentration was 0.17 M for KOH, NaOH, $Na_2CO_3$, and $NaCHO_2$, and 0.085 M for MgO and $Ca(OH)_2$.

The results shown in Table 8 demonstrate that the 2.5% Ru on CTC-120 catalyst is effective with a variety of promoters. In the continuous conversion of sorbitol using a trickle bed reactor under conditions similar to those in Example 5, potassium salts such as KOH, and sodium salts such as NaOH, $Na_2CO_3$, and $NaCHO_2$ were shown to be effective as promoters when used in conjunction with the 2.5% Ru on CTC-120 catalyst. Compare the propylene glycol selectivity for experiments 90726T-S5, 90825T-S3, 90725T-S6, and 90725T-S9 which used KOH, NaOH, $Na_2O_3$, and $NaCH_2O$, respectively, to experiments 90826T-S3 and 90826T-S6 which used MgO and $Ca(OH)_2$, respectively. The results clearly show that selectivity was significantly greater for the sodium and potassium base promoters than for the $Ca(OH)_2$ and MgO promoters.

TABLE 7

| | | | Reaction Parameters | | | | |
|---|---|---|---|---|---|---|---|
| Experiment | Catalyst descript. | Feed Comp. | WHSV (kg/kg cat/hr) | $H_2$:Feed molar ratio | Pressure (psi) | Temp. (° C.) | Promoter Conc. |
| 90706T-S3 | 2.5 wt % | 25 wt % sorbitol | 0.54 | 5.1 | 1200 | 220 | 0.17 M KOH |
| 90706T-S9 | Ru/CTC-120 | 35 wt % sorbitol | 0.54 | 5.1 | 1200 | 220 | 0.24 M KOH |
| 90707T-S3 | carbon | 50 wt % sorbitol | 0.54 | 5.1 | 1200 | 220 | 0.34 M KOH |
| 90712T-S3 | | 70 wt % sorbitol | 0.54 | 5.1 | 1200 | 220 | 0.48 M KOH |

| | Feed Conversion and Product Selectivities | | | | | | | |
|---|---|---|---|---|---|---|---|---|
| Experiment | Feed conversion | PG | EG | Glycerol | $C_4$ | $C_5$ | Lactic acid | Methane |
| 90706T-S3 | 87.1 | 67.0 | 41.4 | 38.5 | 17.3 | 3.4 | 1.5 | 16.2 |
| 90706T-S9 | 84.1 | 72.3 | 44.2 | 31.7 | 16.1 | 2.3 | 2.4 | 10.2 |
| 90707T-S3 | 81.9 | 74.6 | 44.0 | 26.2 | 15.7 | 2.0 | 2.3 | 21.6 |
| 90712T-S3 | 84.6 | 56.7 | 33.3 | 18.7 | 11.1 | 0 | 1.5 | 38.6 |

C4 products are compounds such as 1,2-butanediol, 1,3-butanediol, 1,4-butanediol, and 1,2,4-butanediol.

TABLE 8

Reaction Parameters

| Experiment | Catalyst descript. | Feed Comp. | WHSV (kg/kg cat/hr) | $H_2$:Feed molar ratio | Pressure (psi) | Temp. (° C.) | Promoter Conc. |
|---|---|---|---|---|---|---|---|
| 90726T-S5 | 2.5 wt % Ru/CTC-120 carbon | 25 wt % sorbitol | 0.80 | 5.1 | 1200 | 220 | 0.17 M KOH |
| 90825T-S3 | | 25 wt % sorbitol | 0.80 | 5.1 | 1200 | 220 | 0.17 M NaOH |
| 90725T-S6 | | 25 wt % sorbitol | 0.80 | 5.1 | 1200 | 220 | 0.17 M $Na_2CO_3$ |
| 90725T-S9 | | 25 wt % sorbitol | 0.80 | 5.1 | 1200 | 220 | 0.17 M NaCOOH |
| 90826T-S3 | | 25 wt % sorbitol | 0.80 | 5.1 | 1200 | 220 | 0.085 M MgO |
| 90826T-S6 | | 25 wt % sorbitol | 0.80 | 5.1 | 1200 | 220 | 0.085 M $Ca(OH)_2$ |

Feed Conversion and Product Selectivities

| Experiment | Feed conversion | PG | EG | Glycerol | $C_4$ | $C_5$ | Lactic acid | Methane |
|---|---|---|---|---|---|---|---|---|
| 90726T-S5 | 73.4 | 69.4 | 46.4 | 28.2 | 18.3 | 3.5 | 1.6 | 16.3 |
| 90825T-S3 | 74.7 | 66.0 | 43.3 | 27.6 | 18.1 | 3.3 | 1.9 | 18.6 |
| 90725T-S6 | 72.5 | 69.0 | 47.0 | 28.2 | 17.9 | 3.2 | 1.7 | 18.7 |
| 90725T-S9 | 71.1 | 67.4 | 47.1 | 28.5 | 18.1 | 4.1 | 1.6 | 20.1 |
| 90826T-S3 | 82.5 | 15.1 | 5.7 | 11.0 | 20.0 | 14.6 | 0.3 | 31.6 |
| 90826T-S6 | 73.5 | 15.7 | 6.3 | 20.0 | 22.7 | 22.5 | 0.7 | 32.8 |

C4 products are compounds such as 1,2-butanediol, 1,3-butanediol, 1,4-butanediol, and 1,2,4-butanediol.

EXAMPLE 11

This example was performed to determine whether the amount of ruthenium metal deposited on the CTC-120 support had an effect on conversion of sorbitol to polyols and the selectivity towards propylene glycol, ethylene glycol, and glycerol.

Catalysts comprising 1.5% Ru, 2.5% Ru, or 5.0% Ru on CTC-120 were made as in Example 1 and evaluated for their ability to convert sorbitol in a trickle bed reactor. The conditions for the reactions were similar to those in Example 5 with the following specific parameters. The feedstock sorbitol composition was 25 wt %, the WHSV was 0.80, the hydrogen to feedstock molar ratio was 5 to 1, the pressure was 8.3 MPa (1,200 PSIG), and the promoter was 0.17 M KOH. The temperature was 217° or 231° C. for the 5 wt % Ru on CTC-120; 217° or 231° C. for the 2.5% Ru on CTC-120; and, 231° or 244° C. for the 1.5% Ru on CTC-120.

While the results, shown in Table 9, show that the percent ruthenium comprising the catalyst of the present invention can be from about 1.5% to 5%, the preferred ruthenium concentration is 2.5%. Table 9 shows that a 5% Ru on CTC-120 catalyst was less effective than the 2.5% Ru on CTC-120 catalyst in the continuous conversion of sorbitol to polyols. Table 9 further showed that the 1.5% Ru on CTC-120 catalyst was not significantly less effective than the 2.5% Ru on CTC-120 catalyst in selectivity towards propylene glycol, but displayed lower selectivity towards ethylene glycol and glycerol. Thus, the results in Table 9 show that the optimum catalyst loading onto the CTC-120 carbon support is 2.5 wt %.

TABLE 9

Reaction Parameters

| Experiment | Catalyst descript. | Feed Comp. | WHSV (kg/kg cat/hr) | $H_2$:Feed molar ratio | Pressure (psi) | Temp. (° C.) | Promoter Conc. |
|---|---|---|---|---|---|---|---|
| 90610T-S8 | 5 wt % Ru/CTC-120 carbon | 25 wt % sorbitol | 0.80 | 5.1 | 1200 | 217 | 0.17 M KOH |
| 90616T-S3 | 5 wt % Ru/CTC-120 carbon | 25 wt % sorbitol | 0.80 | 5.1 | 1200 | 231 | 0.17 M KOH |
| 90303T-S9 | 2.5 wt % Ru/CTC-120 carbon | 25 wt % sorbitol | 0.80 | 5.1 | 1200 | 217 | 0.17 M KOH |
| 90303T-S3 | 2.5 wt % Ru/CTC-120 carbon | 25 wt % sorbitol | 0.80 | 5.1 | 1200 | 231 | 0.17 M KOH |
| 90415T-S3 | 1.5 wt % Ru/CTC-120 carbon | 25 wt % sorbitol | 0.80 | 5.1 | 1200 | 231 | 0.17 M KOH |
| 90415T-S5 | 1.5 wt % Ru/CTC-120 carbon | 25 wt % sorbitol | 0.80 | 5.1 | 1200 | 244 | 0.17 M KOH |

Feed Conversion and Product Selectivites

| Experiment | Feed conversion | PG | EG | Glycerol | $C_4$ | $C_5$ | Lactic acid | Methane |
|---|---|---|---|---|---|---|---|---|
| 90610T-S8 | 84.4 | 67.5 | 37.7 | 38.4 | 17.6 | 2.6 | 2.8 | 5.2 |
| 90616T-S3 | 92.0 | 69.6 | 32.4 | 19.5 | 10.1 | 1.0 | 3.7 | 27.4 |
| 90303T-S9 | 63.2 | 75.6 | 51.9 | 50.6 | 15.6 | 0 | 3.3 | 5.1 |
| 90303T-S3 | 77.5 | 71.8 | 48.2 | 38.0 | 15.4 | 3.2 | 3.2 | 11.9 |
| 90415T-S3 | 28.0 | 49.4 | 31.2 | 11.6 | 7.0 | 5.0 | 4.6 | 3.7 |
| 90415T-S5 | 27.3 | 54.8 | 28.7 | 5.9 | 12.2 | 8.7 | 6.3 | 2.9 |

C4 products are compounds such as 1,2-butanediol, 1,3-butanediol, 1,4-butanediol, and 1,2,4-butanediol.

Comparison Example 1

The conversion and selectivities for several commercially available catalysts consisting of other metals were compared to those of the preferred 2.5% Ru on CTC-120 catalyst.

The conditions for the reactions were similar to those in Example 5 with the following specific parameters. The feedstock sorbitol composition was 25 wt %, the WHSV ranged from 0.15 to 0.60, the hydrogen to feedstock molar ratio was 5 to 1, the pressure was 8.3 MPa (1,200 PSIG), and the promoter was 0.17 M KOH. The temperature was 217° or 244° C. for 50 ml of the sintered nickel (Metalyst catalyst) (Degussa, Inc.) and 244° or 258° C. for 50 ml of the 52% Ni/Si/Al$_x$O$_y$ catalyst (United Catalyst).

As shown in Table 10, the two Ni-based catalysts, sintered nickel pellets (Metalyst from Degussa) and nickel supported on silica-alumina (United Catalyst) demonstrated poor selectivities to ethylene glycol, propylene glycol, and glycerol. In contrast, under similar conditions the 2.5% Ru on CTC-120 catalyst has significantly higher selectivities to ethylene glycol, propylene glycol, and glycerol (as shown in Table 5). While these catalysts were less efficacious than the 2.5% Ru on CTC-120 catalyst, these catalysts may be useful as the catalyst for converting sorbitol to polyols in a batch reaction.

EXAMPLE 12

Conversions and selectivities for catalysts containing ruthenium in combination with rhenium on CTC-120 were compared to those of the preferred 2.5% Ru on CTC-120 catalyst. The catalysts which consisted of equal amounts of ruthenium and rhenium were tested under the continuous reaction conditions of Example 5 with specific reaction parameters noted in Table 11 The ruthenium/rhenium catalysts were made as shown in Example 1.

In general, the mixed-metal ruthenium/rhenium catalysts were found to be less effective than the 2.5% Ru on CTC-120 catalyst. As shown in Table 11, the two mixed-metal catalysts, 1.5% Ru/1.5% Re on CTC-120 and 2.5% Ru/2.5% Re on CTC-120, had lower ethylene glycol, propylene glycol, and glycerol selectivities than the 2.5% Ru on CTC-120 catalyst.

TABLE 10

| | | Reaction Parameters | | | | | |
|---|---|---|---|---|---|---|---|
| Experiment | Catalyst descript. | Feed Comp. | WHSV (kg/kg cat/hr) | H$_2$:Feed molar ratio | Pressure (psi) | Temp. (° C.) | Promoter Conc. |
| 90402T-S5 | Sintered Nickel (Metalyst) | 25 wt % sorbitol | 0.15 | 5.1 | 1200 | 217 | 0.17 M KOH |
| 90402T-S3 | Sintered Nickel (Metalyst) | 25 wt % sorbitol | 0.15 | 5.1 | 1200 | 244 | 0.17 M KOH |
| 90408T-S3 | 52% Ni/SiAl$_x$O$_y$ | 25 wt % sorbitol | 0.30 | 5.1 | 1200 | 244 | 0.17 M KOH |
| 90408T-S6 | 52% Ni/SiAl$_x$O$_y$ | 25 wt % sorbitol | 0.60 | 5.1 | 1200 | 258 | 0.17 M KOH |

| | Feed Conversion and Product Selectivities | | | | | | |
|---|---|---|---|---|---|---|---|
| Experiment | Feed conversion | PG | EG | Glycerol | C$_4$ | C$_5$ | Lactic acid | Methane |
| 90402T-S5 | 37.7 | 30.0 | 22.2 | 38.0 | 9.0 | 0 | 3.7 | 49.3 |
| 90402T-S3 | 92.9 | 6.6 | 2.5 | 4.5 | 5.4 | 2.4 | 3.0 | 88.3 |
| 90408T-S3 | 53.4 | 58.4 | 37.5 | 19.9 | 3.5 | 0 | 2.6 | 46.4 |
| 90408T-S6 | 55.5 | 57.3 | 39.0 | 20.4 | 2.1 | 0 | 3.3 | 6.0 |

C4 products are compounds such as 1,2-butanediol, 1,3-butanediol, 1,4-butanediol, and 1,2,4-butanediol.

TABLE 11

| | | Reaction Parameters | | | | | |
|---|---|---|---|---|---|---|---|
| Experiment | Catalyst descript. | Feed Comp. | WHSV (kg/kg cat/hr) | H$_2$:Feed molar ratio | Pressure (psi) | Temp. (° C.) | Promoter Conc. |
| 90603T-S5 | 1.5% Ru/1.5% Re CTC-120 carbon | 25 wt % sorbitol | 0.8 | 5.1 | 1200 | 203 | 0.17 M KOH |
| 90604T-S5 | 1.5% Ru/1.5% Re CTC-120 carbon | 25 wt % sorbitol | 1.6 | 5.1 | 1200 | 203 | 0.17 M KOH |
| 90603T-S3 | 1.5% Ru/1.5% Re CTC-120 carbon | 25 wt % sorbitol | 0.8 | 5.1 | 1200 | 217 | 0.17 M KOH |
| 90517T-S6 | 2.5% Ru/2.5% Re CTC-120 carbon | 25 wt % sorbitol | 0.8 | 5.1 | 1200 | 203 | 0.17 M KOH |
| 90601T-S6 | | 25 wt % sorbitol | 1.6 | 5.1 | 1200 | 217 | 0.17 M KOH |

TABLE 11-continued

| | | | | | | | |
|---|---|---|---|---|---|---|---|
| 90326T-S3 | 2.5% Ru CTC-120 carbon | 25 wt % sorbitol | 0.8 | 5.1 | 1200 | 203 | 0.17 M KOH |
| 90326T-S6 | 2.5% Ru CTC-120 carbon | 25 wt % sorbitol | 1.0 | 5.1 | 1200 | 203 | 0.17 M KOH |
| 90303T-S9 | 2.5% Ru CTC-120 carbon | 25 wt % sorbitol | 0.80 | 5.1 | 1200 | 217 | 0.17 M KOH |

| | Feed Conversion and Product Selectivites | | | | | | |
|---|---|---|---|---|---|---|---|
| Experiment | Feed conversion | PG | EG | Glycerol | $C_4$ | $C_5$ | Lactic acid | Methane |
| 90603T-S5 | 90.7 | 32.9 | 18.6 | 29.0 | 16.2 | 5.0 | 2.1 | 16.5 |
| 90604T-S5 | 65.7 | 46.9 | 34.3 | 56.1 | 29.7 | 11.4 | 3.2 | 5.5 |
| 90603T-S3 | 97.8 | 27.2 | 8.9 | 14.4 | 15.1 | 3.4 | 2.0 | 23.4 |
| 90517T-S6 | 89.7 | 33.5 | 15.3 | 31.2 | 15.5 | 7.6 | 2.0 | 21.8 |
| 90601T-S6 | 55.1 | 42.0 | 30.1 | 52.7 | 34.0 | 13.3 | 1.7 | 6.7 |
| 90326T-S3 | 65.0 | 74.2 | 46.2 | 52.6 | 17.7 | 0 | 3.9 | 4.2 |
| 90326T-S6 | 60.9 | 74.9 | 47.1 | 49.4 | 17.3 | 0 | 3.6 | 2.5 |
| 90303T-S9 | 63.2 | 75.6 | 51.9 | 50.6 | 15.5 | 0 | 3.3 | 5.0 |

C4 products are compounds such as 1,2-butanediol, 1,3-butanediol, 1,4-butanediol, and 1,2,4-butanediol.

EXAMPLE 14

The longevity of the 2.5% Ru on CTC-120 catalyst under continuous reaction conditions was measured.

The reactions were performed as in Example 5 with particular differences noted in Table 12. As shown in Table 12, the 2.5% Ru on CTC-120 catalyst was stable for over 1,000 hours without any type of regeneration of the catalyst being required. Furthermore, not only did the catalyst display remarkably enhanced longevity in the reaction but also the conversion and selectivity to the desired ethylene glycol and propylene glycol products increased over the same time period. The most dramatic increase was seen for propylene glycol. In contrast, the selectivity for glycerol decreased over the same time period. Therefore, the 2.5% Ru on CTC-120 catalyst has a longevity in a continuous conversion reaction that greatly exceeds the catalysts of the prior art.

TABLE 12

Results of Extended Catalyst Run

| Run | 1 | 2 | 3 | 4 | 5 | 6 | 7 |
|---|---|---|---|---|---|---|---|
| Hours on catalyst | 34 | 7 | 287 | 720 | 1025 | 1139 | 1163 |
| temperature | 220 | 220 | 220 | 220 | 250 | 240 | 240 |
| Pressure (psi) | 1200 | 1200 | 1200 | 1200 | 1200 | 1200 | 1200 |
| Flow (ml/hour) | 33 | 33 | 33 | 33 | 60 | 50 | 50 |
| Sorbitol % | 24.6 | 24.6 | 24.6 | 24.6 | 24.1 | 24.1 | 24.1 |
| Contact time | 1.21 | 1.21 | 1.21 | 1.21 | 0.667 | 0.8 | 0.8 |
| Hydrogen to feed ratio | 5.07 | 5.04 | 5.07 | 5.07 | 5.07 | 4.2 | 4.2 |
| Conversion % | 81.8 | 81.4 | 83.8 | 88.3 | 95.3 | 93.9 | 94.0 |
| Glycerol | 40.6 | 43.3 | 42.7 | 41.9 | 20.42 | 27.0 | 26.9 |
| Ethylene glycol | 42.4 | 44.6 | 45.3 | 43.0 | 44.3 | 45.2 | 45.5 |
| propylene glycol | 66.4 | 68.1 | 68.5 | 67.2 | 75.6 | 74.4 | 74.9 |

C4 products are compounds such as 1,2-butanediol, 1,3-butanediol, 1,4-butanediol, and 1,2,4-butanediol.

While the present invention is described herein with reference to illustrated embodiments, it should be understood that the invention is not limited hereto. Those having ordinary skill in the art and access to the teachings herein will recognize additional modifications and embodiments within the scope thereof. In particular, those skilled in the art will appreciate that larger quantities of catalyst can be made by the same process disclosed herein by scaling the quantities of reagents to any desired level. Furthermore, those skilled in the art will appreciate that the conversion reactions disclosed herein for producing low molecular weight polyols from sugar alcohols or high molecular weight polyols can be scaled to any desired level and can use sugar alcohols or high molecular weight polyols derived from a variety of sources, which include, but are not limited to, plant material, microbial fermentation or production, and chemical synthesis. Therefore, the present invention is limited only by the claims attached herein.

We claim:

1. A process for preparation of low molecular weight polyols which comprises:
  (a) providing a transition metal catalyst prepared by depositing a transition metal salt in a solvent on an inert support, drying to remove the solvent, reducing the metal salt to the metal with hydrogen, and passivating the metal in an oxygen containing atmosphere so as to provide an oxide of the metal on the surface of the metal in a reaction vessel;
  (b) reacting the catalyst with hydrogen in the vessel;
  (c) providing in the vessel a reaction mixture of a high molecular weight polyol in water and a base promoter;
  (d) reacting the reaction mixture containing the base with the catalyst and hydrogen at an elevated temperature and hydrogen pressure wherein the temperature is between 180° C. and 250° C. and the hydrogen pressure is between about 3.4 to 14 MPa (500 to 2,000 PSIG) to produce low molecular weight polyols in the reaction mixture;

(e) removing the reaction mixture with the lower molecular weight polyols from the vessel;

(f) recovering the low molecular weight polyols from the reaction mixture along with unreacted hydrogen; and (g) separating the unreacted hydrogen from the reaction mixture and purifying to greater than 90% by volume hydrogen with the removal of methane; and (h) recycling the purified hydrogen to the reaction mixture.

2. The process of claim 1 wherein the inert support is selected from the group consisting of alumina, titania, and microporous carbon.

3. The process of claims 1 or 2 wherein the transition metal is ruthenium.

4. A process for preparation of a mixture of ethylene glycol and propylene glycol which comprises:

(a) providing a ruthenium metal catalyst prepared by depositing a ruthenium metal salt in a solvent on an inert support, drying to remove the solvent, reducing the ruthenium metal salt to ruthenium metal with hydrogen, and passivating the ruthenium metal in an oxygen containing atmosphere so as to provide an oxide of the metal on the surface of the metal in a reaction vessel;

(b) reacting the catalyst with hydrogen in the vessel;

(c) providing to the vessel a reaction mixture of a high molecular weight polyol in water and a base promoter;

(d) reacting in the vessel the reaction mixture containing the base with the catalyst and hydrogen at an elevated temperature and hydrogen pressure, wherein the base is present in an amount between 0.02 and 0.3 moles per liter, the hydrogen pressure is between about 3.4 to 14 MPa (500 to 2,000 PSIG), the mixture of polyols is between 5% to 70% by weight in water, the temperature is between 180° C. and 250° C. to produce the ethylene glycol and propylene glycol in the reaction mixture;

(e) removing the reaction mixture with the lower molecular weight polyols from the vessel along with gases generated in the reaction and unreacted hydrogen;

(f) recovering the low molecular weight polyols from the reaction mixture, and (g) separating the unreacted hydrogen from the reaction mixture and purifying to greater than 90% by volume hydrogen with the removal of methane; and (h) recycling the purified hydrogen to the reaction mixture.

5. The process of claim 4 wherein the vessel is sealed.

6. The process of claim 4 wherein the vessel is a column with continuous flow through the column of the reaction mixture over the catalyst and wherein a weight hourly space velocity is between about 0.3 and 3.

7. The process of any one of claims 4, 5 or 6 wherein the inert support is selected from the group consisting of alumina, titania, and microporous carbon.

8. The process of any one of claims 4, 5 or 6 wherein the inert support is a microporous carbon having a greater than 0.6 cc per gram of microporous void volume.

9. The process of any one of claims 4, 5 or 6 wherein the inert support is a microporous carbon derived from coconuts.

10. The process of any one of claims 4, 5 or 6 wherein the base is selected from the group consisting of alkali metal bases and salts.

11. The process of claim 4 wherein the ratio of hydrogen to polyols in step (e) is between about 1.4 to 1 and 8.7 to 1.

12. A process for preparation of a mixture of ethylene glycol and propylene glycol which comprises:

(a) providing a ruthenium metal catalyst prepared by depositing a ruthenium metal salt in a solvent on an inert support, drying to remove the solvent, reducing the ruthenium metal salt to ruthenium metal with hydrogen, and passivating the ruthenium metal in an oxygen containing atmosphere so as to provide an oxide of the metal on the surface of the metal in a reaction vessel;

(b) reacting the catalyst with hydrogen in the vessel;

(c) providing to the vessel a reaction mixture of a high molecular weight polyol in water and a base promoter;

(d) reacting in the vessel the reaction mixture containing the base with the catalyst and hydrogen at an elevated temperature and hydrogen pressure, wherein the base is present in an amount between 0.02 and 0.3 moles per liter, the pressure is between about 3.4 to 14 MPa (500 to 2,000 PSIG), the mixture of polyols is between 5% to 70% by weight in water, the temperature is between 180° C. and 250° C. to produce the ethylene glycol and propylene glycol in the reaction mixture;

(e) removing the reaction mixture with the lower molecular weight polyols from the vessel; and (f) introducing the reaction mixture into a separator for separating liquid from gases generated in the reaction and the hydrogen which are in turn separated with return of the hydrogen to the reaction mixture and wherein the separated liquid is demineralized to remove inorganic components and then the propylene glycol and ethylene glycol are recovered from the liquid.

13. The process of claim 12 wherein some water is removed from the liquid upon removal of the ethylene glycol and propylene glycol to produce a recycle mixture which is added to the reaction mixture along with the base.

14. The process of any one of claims 1, 2, 3, 4, 12 or 13 wherein the base promoter is selected from the group consisting of alkali metal bases and salts.

15. The process of any one of claims 1, 2, 3, 4, 12 or 13 wherein the base promoter is selected from the group consisting of potassium hydroxide, sodium hydroxide, sodium formate, and sodium carbonate.

16. The process of any one of claims 1, 2, 3, 4, 12 or 13 wherein the high molecular weight polyol is selected from the group consisting of xylitol, arabinitol, and sorbitol.

17. A process for preparation of low molecular weight polyols which comprises:

(a) providing a transition metal catalyst prepared by depositing a transition metal salt in a solvent on an inert support, drying to remove the solvent, reducing the metal salt to the metal with hydrogen, and passivating the metal in an oxygen containing atmosphere so as to provide an oxide of the metal on the surface of the metal in a reaction vessel;

(b) reacting the passivated catalyst with hydrogen in the vessel;

(c) providing to the vessel a reaction mixture of a high molecular weight polyol in water and a base promoter;

(d) reacting the reaction mixture containing the base with the catalyst and hydrogen at an elevated temperature and elevated hydrogen pressure to produce low molecular weight polyols in the reaction mixture;

(e) removing the reaction mixture with the lower molecular weight polyols from the vessel;

(f) recovering the low molecular weight polyols from the reaction mixture, and (g) separating the unreacted hydrogen from the reaction mixture and purifying to greater than 90% by volume hydrogen with the removal of methane; and (h) recycling the purified hydrogen to the reaction mixture.

18. A process for preparation of low molecular weight polyols which comprises:
(a) providing a passivated transition metal catalyst comprising a transition metal on an inert support wherein the dispersion of the transition metal increases over time in a hydrogenolysis reaction in a reaction vessel;
(b) reacting the passivated catalyst with hydrogen in the vessel;
(c) providing to the vessel a reaction mixture of a high molecular weight polyol in water and a base promoter;
(d) reacting the reaction mixture containing the base with the catalyst at elevated temperature and elevated hydrogen pressure to produce low molecular weight polyols in the reaction mixture;
(e) removing the reaction mixture with the lower molecular weight polyols from the vessel; and,
(f) recovering the low molecular weight polyols from the reaction mixture.

19. The process of claim 18 wherein the passivated transition metal catalyst is prepared by depositing a transition metal salt in a solvent on an inert support, drying to remove the solvent, reducing the metal salt to the metal with hydrogen, and passivating the metal in an oxygen containing atmosphere so as to provide an oxide of the metal on the surface of the metal.

20. The process of claim 18 or 19 wherein the inert support is selected from the group consisting of alumina, titania, and microporous carbon.

21. The process of claim 18 or 19 wherein the inert support has a BET surface area between about 1 to 1,000 m$^2$ per gram.

22. The process of claim 18 or 19 wherein the transition metal is ruthenium between about 1.5 to 5.0 wt %.

23. A process for preparation of low molecular weight polyols which comprises:
(a) providing a passivated transition metal catalyst comprising a transition metal on an inert support in a reaction vessel;
(b) reacting the passivated catalyst with hydrogen in the vessel;
(c) providing in the vessel a reaction mixture of a high molecular weight polyol in water and a base promoter;
(d) reacting the reaction mixture containing the base with the catalyst and hydrogen at elevated temperature and elevated hydrogen pressure to produce low molecular weight polyols in the reaction mixture;
(e) removing the reaction mixture with the lower molecular weight polyols from the vessel;
(f) recovering the low molecular weight polyols from the reaction mixture along with the unreacted hydrogen; and
(g) separating the unreacted hydrogen from the reaction mixture and purifying to greater than 905 by volume hydrogen with the removal of methane; and
(h) recycling the purified hydrogen to the reaction mixture.

* * * * *

UNITED STATES PATENT AND TRADEMARK OFFICE
CERTIFICATE OF CORRECTION

PATENT NO. : 6,291,725 B1
DATED : September 18, 2001
INVENTOR(S) : Shubham P. Chopade, Dennis J. Miller, James E. Jackson, Todd A. Werpy, John G. Frye, Jr. and Alan H. Zacher It is certified that error appears in the above-identified patent and that said Letters Patent is hereby corrected as shown below:

Title page,
Under "OTHER PUBLICATIONS" line 6, "Brunauer, emmett" should be
-- Brunauer, Emmett --.

Column 13,
Line 25, "rated tI pressure" should be -- rated pressure -- .

Column 15, Table 4,
Line 5 of Table, "5 wt % Ru" should be -- 5 wt % Ru/C --.

Column 17, Table 5,
Under the heading "PG", "6.7" should be -- 69.7 --.

Column 26, Table 12,
Under column heading "2", "7" should be -- 79 --.

Signed and Sealed this

Ninth Day of April, 2002

Attest:

JAMES E. ROGAN
*Attesting Officer*  *Director of the United States Patent and Trademark Office*